United States Patent [19]

Hirai et al.

[11] Patent Number: 4,839,365
[45] Date of Patent: Jun. 13, 1989

[54] THIENOPYRIDINE DERIVATIVES USEFUL IN TREATING GASTRIC ULCERS

[75] Inventors: Kentaro Hirai, Kyoto; Yukio Mizushima; Masami Doteuchi, both of Osaka, all of Japan

[73] Assignee: Shinogi & Co., Ltd., Osaka, Japan

[21] Appl. No.: 191,057

[22] Filed: May 6, 1988

[30] Foreign Application Priority Data

May 19, 1987 [JP] Japan .................. 62-122217

[51] Int. Cl.⁴ .................. A61K 31/44; C07D 495/04
[52] U.S. Cl. ....................... 514/301; 546/114
[58] Field of Search ............... 546/114; 514/301

[56] References Cited

FOREIGN PATENT DOCUMENTS 0130729  1/1985  European Pat. Off. .
0176308  4/1986  European Pat. Off. .
0251294  1/1988  European Pat. Off. .

*Primary Examiner*—Mary C. Lee
*Assistant Examiner*—Bernard I. Dentz
*Attorney, Agent, or Firm*—Wenderoth, Lind & Ponack

[57] ABSTRACT

A compound of the formula:

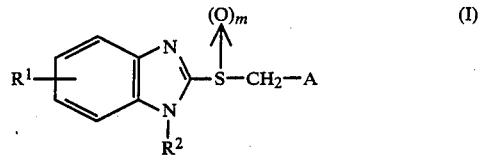

(wherein $R^1$ is hydrogen, $C_1$–$C_5$ alkyl, $C_1$–$C_5$ alkoxy, $C_1$–$C_5$ alkoxycarbonyl, or trifluoromethyl; $R^2$ is hydrogen, $C_1$–$C_5$ alkoxycarbonyl, $C_6$–$C_{12}$ aryloxycarbonyl, $C_1$–$C_5$ alkanoyloxy-$C_1$–$C_5$ alkyl, $C_1$–$C_5$ alkoxycarbonyloxy-$C_1$–$C_5$ alkyl, $C_1$–$C_5$ acylamino-$C_1$–$C_5$ alkyl, 2-hydroxy-1-$C_2$–$C_5$ alkenyl, phthalimido-$C_1$–$C_5$ alkyl, halogeno-$C_1$–$C_5$ alkoxycarbonyl-$C_1$–$C_5$ alkyl, hydroxy-$C_1$–$C_5$ alkyl, $C_1$–$C_5$ alkylthio-$C_1$–$C_5$ alkyl, or $C_1$–$C_5$ alkylsulfinyl-$C_1$–$C_5$ alkyl;

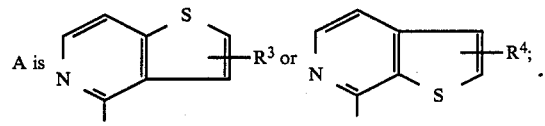

m is an integer of 0 or 1; $R^3$ and $R^4$ each is hydrogen, halogen, cyano, $C_1$–$C_5$ alkyl, amino, $C_1$–$C_5$ alkoxy, $C_6$–$C_{12}$ aryl-$C_1$–$C_5$ alkoxy, $C_1$–$C_5$ alkoxycarbonyl, fluoro-$C_1$–$C_5$ alkoxy, $C_1$–$C_5$ alkanoylamino, or carbamoyl) or its salt, being useful as antiulcer agents, is provided.

4 Claims, No Drawings

THIENOPYRIDINE DERIVATIVES USEFUL IN TREATING GASTRIC ULCERS

BACKGROUND OF THE INVENTION

The present invention relates to thienopyridine derivatives. More particularly, this invention is directed to thienopyridine derivatives which have been found to be particularly available as an antiulcer agent, to their preparation, to their use, and to pharmaceutical formulations containing the compounds.

Benzimidazole derivatives being useful as antiulcer agents have heretofore been known, for example, in U.S. Pat. No. 4,255,431 and EP Unexamd. Pat. Publn. No. 176308-A.

The inventors of the present invention have been studying on antiulcer agents of the benzimidazole family including the copmounds, as in EP Unexamd. Pat. Publn. No. 251294-A. Further they have found that the thienopyridine derivatives have excellent antiulcer activities.

SUMMARY OF THE INVENTION

According to the present invention, there is provdied a thienopyridine of the formula:

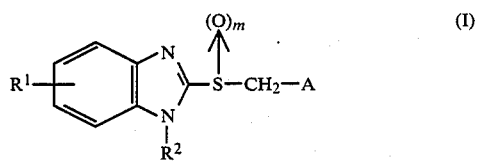

(wherein $R^1$ is hydrogen, $C_1$-$C_5$ alkyl, $C_1$-$C_5$ alkoxy, $C_1$-$C_5$ alkoxycarbonyl, or trifluoromethyl; $R^2$ is hydrogen, $C_1$-$C_5$ alkoxycarbonyl, $C_5$-$C_{12}$ aryloxycarbonyl, $C_1$-$C_5$ alkanoyloxy-$C_1$-$C_5$ alkyl, $C_1$-$C_5$ alkoxycarbonyloxy-$C_{1-5}$ alkyl, $C_{1-5}$ acylamino-$C_{1-5}$ alkyl, 2-hydroxy-1-$C_2C_5$ alkenyl, phthalimido-$C_1C_5$ alkyl, halogeno-$C_{1-5}$ alkoxycarbonyl-$C_{1-5}$ alkyl, hydroxy-$C_1C_5$ alkyl, $C_{1-5}$ alkylthio$C_{1-5}$ alkyl, or $C_{1-5}$ alkylsulfinyl-$C_{1-5}$ aklyl;

A is

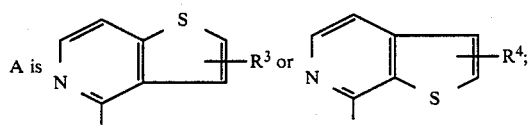

m is an integer of 0 or 1; $R^3$ and $R^4$ each is hydrogen, halogen, cyano, $C_1$-$C_5$ alkyl, amino, $C_{1-5}$ alkoxy, $C_{5-12}$ aryl-$C_{1-5}$ alkanoylamino, or carbamoyl) or its salt.

The terms used in the above mentioned definition are explained as follows:

As the alkyl, methyl, ethyl, n-propyl, isopropyl, n-butyl, sec-butyl, sio-butyl, tert-butyl, n-pentyl, iso-pentyl, secpentyl, neo-pentyl and tert-pentyl are exemplified.

As the alkoxy, methoxy, ethoxy, n-propoxy, isopropoxy, n-butoxy, sec-butoxy, isobutoxy, tert-butoxy, n-pentyloxy, isopentyloxy, sec-pentyloxy, neo-pentyloxy, and tert-pentyloxy are exemplified.

As the alkoxycarbonyl, methoxycarbonyl, ethoxycarbonyl, propoxycarbonyl, butoxycarbonyl, and pentyloxycarbonyl are exemplified.

As the aryloxycarbonyl, phenyloxycarbonyl, tolyloxycarbonyl, and naphthyloxycarbonyl are exemplified.

As the alkanoyloxyalkyl, acetyloxymethyl, acetyloxyethyl, propionyloxymethyl, propionyloxyethyl, and valeryloxymethyl are exemplified.

As the alkoxycarbonyloxyalkyl, methoxycarbonyloxymethyl, ethoxycarbonyloxymethyl, and propoxycarbonyloxyethyl are exemplified.

As the acylaminoalkyl, acetylaminomethyl, and propionylaminopropyl are exemplified.

As the 2-hydroxy-1-alkenyl, 2-hydroxyl-1-ethenyl, and 2-hydroxy-1-propenyl are exemplified.

As the phthalimidoalkyl, phthalimidomethyl, phthalimidoethyl, and phthalimidopropyl are exemplified.

As the halogenoalkoxycarbonylalkyl, chloromethoxycarbonylmethyl, and bromoethoxycarbonylmethyl are illustrated.

As the hydroxyalkyl, hydroxymethyl, hydroxyethyl, and hydroxypropyl are illustrated.

As the alkylthioalkyl, methylthiomethyl, ethylthiomethyl, methylthioethyl, and methylthiobutyl are illustrated.

As the alkylsulfinylalkyl, methylsulfinylmethyl, ethylsulfinylmethyl, and ethylsulfinylpropyl are illustrated.

As the halogen, fluorine, chlorine, bromine, and iodine are illustrated.

As the arylalkoxy, benzyloxy, phenylethyloxy and phenylpropyloxy are illustrated.

As the fluoroalkyl, fluoromethyl, fluoroethyl, and trifluoromethyl are illustrated.

As the alkanoylamino, formylamino, acetylamino, propionylamino, and butyrylamino are exemplified.

The compound of the present invention have an excellent antiulcer activity, and they are available for medicines or verterinary medicines. Accordingly the invention also provides a pharmaceutical composition comprising as an active ingredient 0.1 to 95 % by weight of at least a compound of the formula (I) associated with a pharmaceutically acceptable carrier, diluent and/or excipient. Compound (I) of the present invention is produced by the following method:

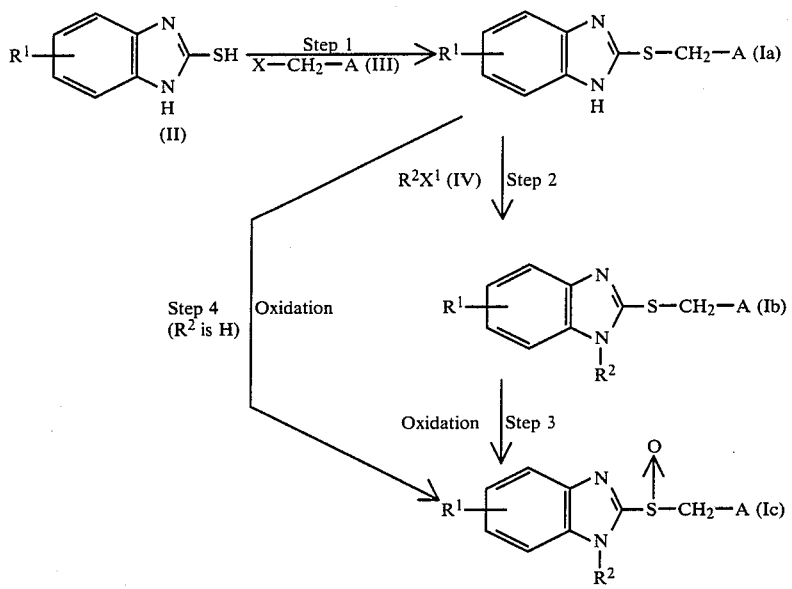

(wherein $R^1$, $R^2$ and A have the same meaning as defined above; X and $X^1$ each is halogen).

Step 1

Compound (II) is allowed to react with the halomethylthienopyridine compound (III) in the presence of a base in an appropriate solvent, whereby Compound (Ia) is obtained.

As the solvent, aromatic solvents (such as benzene, toluene, xylene or the like), alkanols (such as methanol, ethanol, isopropanol or the like), ethers (such as tetrahydrofuran, dibutyl ether or the like), dimethylformamide and dimethyl sulfoxide can be used.

As the base, alkali hydroxides (such as sodium hydroxide or potassium hydroxide), sodium hydrogencarbonate, potassium carbonate, triethylamine, N-methylmorpholine, piperidine, pyrrolidine, pyridine, etc. can be used.

When the reaction is performed at a temperature from around room temperature (about 5°–30° C., hereinafter similarly applicable) to a temperature of refluxing the solvent with heating, the reaction is completed within several ten minutes to several hours.

Step 2

Compound (Ia) obtained in the above step is a first converted into its salt of a alkali metal by reacting with alkali metal hydride such as sodium hydride or potassium hydride in an appropriate solvent such as dimethylformamide; and then the salt is allowed to react with the reagent (IV) including $R^2$ portion in an appropriate solvent, whereby Compound (Ib) is obtained.

As the solvent, those mentioned in Step 1 are exemplified. The reaction is performed at a temperature from under ice-cooling (about —15° to 10° C., hereinafter similarly applicable) to around room tempertaure and completed within several ten minutes to several hours. Compound (Ib) can also be obtained (when $R^2$ is $CH_2OH$) by making Compound (Ia) react with formaldehyde in a solvent such as acetonitrile. In this method, the reaction may be performed at a temperature from about 15° to 100° C.

Step 3

Then, Compound (Ib) is allowed to react with a peracid in an appropriate solvent, whereby Compound (Ic) is obtained. As the solvent, chloroform and carbon tetrachloride are exemplified. If necessary, methanol may be added thereto.

As the peracid, peracetic acid, perbenzoic acid, and m-chloroperbenzoic acid are exemplified.

The reaction is performed at a temperature from under ice-cooling to around room temperature and completed within several ten minutes to several hours.

Step 4

Compound (Ic) can also be obtained by reacting Compound (Ia) (when $R^2$ is hydrogen) with a peracid. The reaction is performed as in Step 3.

For example, the starting material (III) can be obtained by a synthetic process as shown in the undermentioned chart. It is referred to Dressler et al. J. Heterocyclic Chem., 7, 1257–1268 (1970).

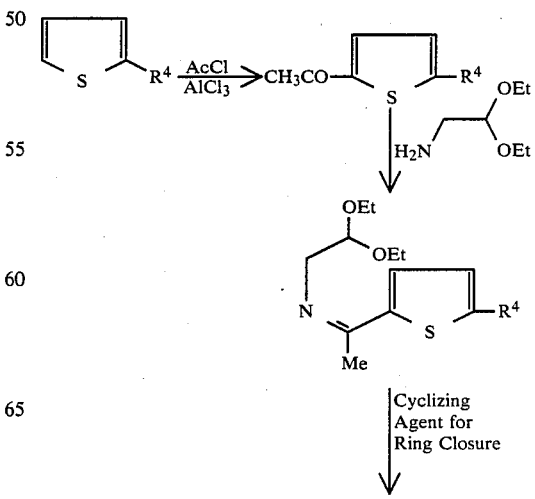

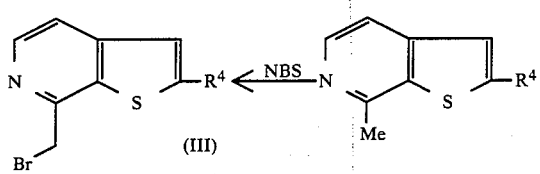

(wherein R⁴ has the same meaning as defined above).

The objective compound (I) of the present invention can be converted into its acid addition salt. In this case, the usable acids include inorganic acids such as hydrochloric acid, hydrobromic acid and phosphoric acid, and organic acids such as acetic acid, oxalic acid, maleic acid, fumaric acid, citric acid, malic acid, adipic acid, succinic acid, 3-chlorobenzoic acid and benzoic acid. The objective compound (I) of the present invention and/or its salt can be administered orally or parenterally to humans or animals. For instance, Compound (I) is administered orally in the form of tablet, granule, powder, capsule or solution and parenterally in the form of injection or suppository. These preparations are manufactured by well known methods using various additives such as excipient, binder, disintegrator, lubricant, stabilizer, taste- or odor-corrective, suspending agent, dispersant, solubilizer and preservative. As the excipient, lactose, sucrose, starch, cellulose, sorbitol, etc.; and as the binder, gum arabic, gelatin, polyvinylpyrrolidone, etc.; and as the lubricant, magnesium stearate, talc, silica gel, etc. are exemplified. In the application of the objective compound (I) of the present invention for the treatment of peptic ulcer in human adults, it is advisable to administer it orally or parenterally once or several times a day at a dosage of about 0.1–100 mg/kg.

The following Examples, Referential Examples and Formulation are shown to clarify embodiments of this invention.

The abbreviations used in the Examples, Referential Examples and Tables have the following meanings: Me: Methyl; Et: Ethyl; t-Bu: t-Butyl; DMF: Dimethylformamide; NBS: N-bromosuccinimide; m-CPBA: m-Chloroperbenzoic acid; AcOEt: Ethyl acetate; CLCOOEt: Ethyl chlorocarbonate; MeOH: Methanol; TsCl: p-Tosyl chloride; Ph: Phenyl; AIBN: 2,2′-azobisisobutyronitrile; PPA: Polyphosphoric acid; AcCl: Acetyl chloride; HBr: Hydrobromic acid; (d): Decomposition point.

EXAMPLE 1

Synthesis of 2-[(thieno[2,3-c]pyridin-7-yl)methylthio]benzimidazole (Ia-1)

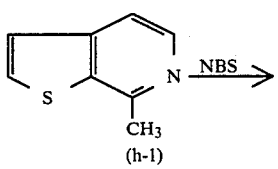

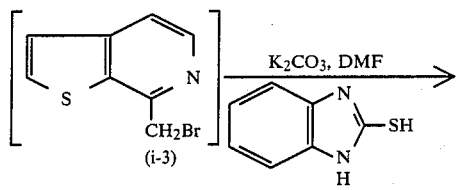

To 5.18 g (34.7 mmol) of 7-methylthieno[2, 3-c]pyridine were added 217 ml of carbon tetrachloride, 9.88 g (55.5 mmol) of N-bromosuccinimide and 91.1 mg (0.555 mmol) of 2,2′-azobisisobutyronitrile, and the mixture was refluxed for 3 hr. The mixture was cooled to room temperature, and after separating the insoluble material by filtration, the filtrate was concentrated, and subjected to silica gel column chromatography for purification, whereby a solution of 7-bromomethylthieno[2, 3-c]pyridine (i-3) was obtained. Compound (i-3) is stable in solution, but it decomposes without solvent.

NMRδ (CDCl₃): 4.83 (s, 2H); 7.40 (d, 1H); 7.65 (d, 1H); 7.73 (d, 1H); 8.48 (d, 1H)

To the solution of Compound (i-3) were added 2.10 g (14.0 mmol) of 2-mercaptobenzimidazole, 9.67 g (70.0 mmol) of K₂CO₃, and 98 ml of dry DMF, and the mixture was stirred for 1 hr at room temperature. After evaporating DMF under reduced pressure, water was added to the residue, and the mixture was filtered and extracted with CH₂Cl₂. The CH₂Cl₂ layer was washed with 10% aqueous solution of K₂CO₃, dried over anhydrous sodium sulfate and concentrated under reduced pressure, whereby 2.70 g of pale yellow crystals were obtained. After silica gel column chromatography, the produce was dispersed in 10 ml of ether, followed by filtration and washed with ether, whereby 2.48 g of the objective compound (Ia-1) was obtained (Yield : 24.0%).

Melting point: 195.0 - 196.0° C. (d)
Anal. Calcd. (%) for C₁₅H₁₁N₃S₂.1/10H₂O :C, 60.22; H, 3.77; N, 14.04; S, 21.43.
Found (%) :C, 60.29; H, 3.91; N, 13.99; S, 21.23.

EXAMPLES 2-5

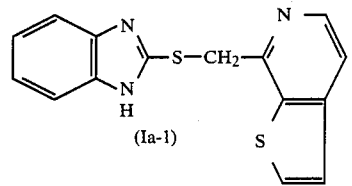

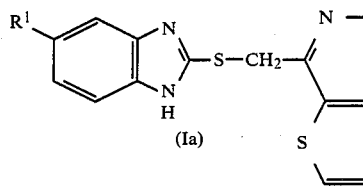

(wherein $R^1$ has the same meaning as defined above)

The reactions were performed under the conditions shown in Table 1 as in Example 1, whereby the objective compounds (Ia) were obtained.

0.5 ml of 10% aqueous solution of sodium sulfite were added to the solution, and the mixture was warmed up to room temperature, added with water and extracted with $CHCl_3$. After drying over anhydrous sodium sulfate, the solvent was evaporated under reduced pressure, whereby 387.7 mg of dark brown viscous liquid was obtained. After silica gel column chromatography, the crystals were dispersed with 3 ml of AcOEt, followed by filtration and washed with AcOEt, whereby 173.5 mg (Yield : 61.0%) of the objective compound (Ic-1), 2-[(thieno[2,3-c]pyridin-7-yl)methylsulfinyl]benzimidazole was obtained as crystals.

Melting point : 163 - 163.5° C. (d) (colored from 145° C.)

TABLE 1

| Ex No. | Compd. No. | $R^1$ | Amount of (h-1) (g) (mmol) | Yield of (Ia) (g) (Yield: %) | M.P. (°C.) | Molecular Formula | Elementary Analysis (%) Up: Calcd. Down: Found | | | | |
|---|---|---|---|---|---|---|---|---|---|---|---|
| | | | | | | | C | H | N | S | F |
| 2 | Ia-2 | Me | 1.34 (9.00) | 0.7577 (26.5) | Amorphous | $C_{16}H_{13}N_3S_2 \cdot \frac{1}{3} H_2O$ | 60.54 60.35 | 4.34 4.53 | 13.24 13.46 | 20.20 19.98 | |
| 3 | Ia-3 | MeO | 1.34 (9.00) | 0.7911 (26.5) | Amorphous | $C_{16}H_{13}N_3OS_2 \cdot \frac{1}{4} H_2O$ | 57.90 57.90 | 4.10 4.29 | 12.66 12.95 | 19.32 19.25 | |
| 4 | Ia-4 | COOMe | 1.34 (9.00) | 0.8356 (25.7) | 169.0-172.5 (d) | $C_{17}H_{13}N_3O_2S_2 \cdot \frac{1}{3} H_2O$ | 56.49 56.58 | 3.81 3.95 | 11.63 11.61 | 17.74 17.73 | |
| 5 | Ia-5 | $CF_3$ | 1.34 (9.00) | 0.7614 (22.9) | 180.5-182.0 (d) | $C_{16}H_{10}N_3F_3S_2 \cdot \frac{1}{4} H_2O$ | 51.95 51.93 | 2.86 2.98 | 11.36 11.46 | 17.33 17.48 | 15.41 15.58 |

EXAMPLE 6

Synthesis of 2-[(thieno[2,3-c]pyridin-7-yl)methylsulfinyl]benzimidazole (Ic-1)

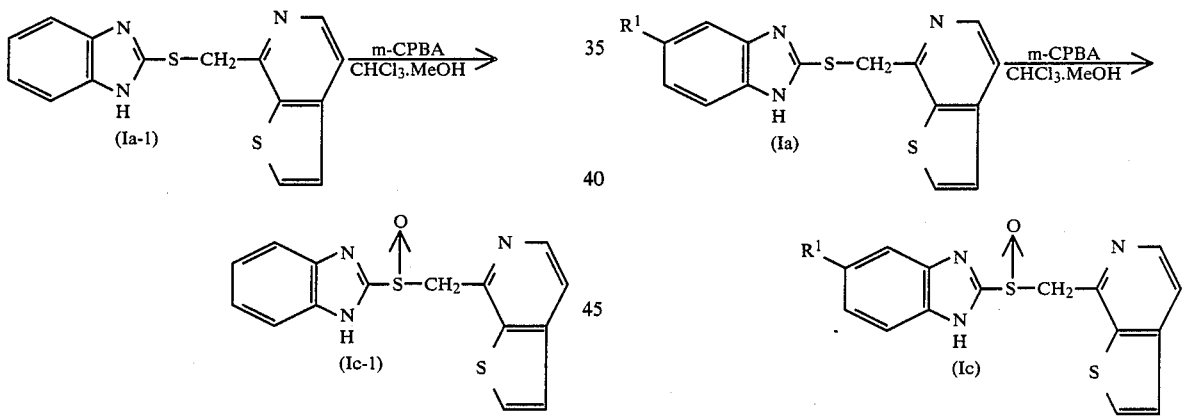

To a solution of 269.3 mg (0.900 mmol) of 2-[(thieno[2,3-c]pyridin-7-yl)methylthio]benzimidazole. 1/10 $H_2O$ (Ia-1) of $CHCl_3$-MeOH (20 ml/ 1 ml) was added 194.1 mg (0.900 mmol) of 80% m-CPBA at −10° to −15° C., and the mixture was stirred for 30 minutes. A saturated aqueous solution of $NaHCO_3$ (2.5 ml) and Anal. Calcd. (%) for $C_{15}H_{11}N_3OS_2 1/7\ N_2O$ : C, 57.02; H, 3.60; N, 13.30; S, 20.29.
Found (%) : C, 57.02; H, 3.79; N, 13.24; S, 20.19.

EXAMPLES 7-10

(wherein $R^1$ has the same meaning as dfined above).

The reactions were performed under the conditions shown in Table 2 as in Example 2, whereby the objective compounds (Ic) were obtained.

TABLE 2

| Ex No. | Compd. No. | $R^1$ | Amount of (Ia) (mg) (mmol) | Yield of (Ic) (mg) (Yield: %) | M.P. (°C.) | Molecular Formula | Elementary Analysis (%) Up: Calcd. Down: Found | | | | |
|---|---|---|---|---|---|---|---|---|---|---|---|
| | | | | | | | C | H | N | S | F |
| 7 | Ic-2 | Me | 317.4 ($\frac{1}{3} H_2O$) (1.00) | 285.6 (84.4) | Amorphous | $C_{16}H_{13}N_3OS_2 \cdot 3/5\ H_2O$ | 56.82 56.87 | 4.23 4.25 | 12.42 12.14 | 18.96 18.88 | |
| 8 | Ic-3 | MeO | 331.9 ($\frac{1}{4} H_2O$) (1.00) | 294.4 (84.3) | Amorphous | $C_{16}H_{13}N_3O_2S_2 \cdot \frac{1}{3} H_2O$ | 55.00 54.89 | 3.94 4.09 | 12.03 11.89 | 18.35 18.14 | |
| 9 | Ic-4 | COOMe | 361.4 ($\frac{1}{3} H_2O$) (1.00) | 347.9 (92.9) | 171.5-172.0 (d) | $C_{17}H_{13}N_3O_3S_2 \cdot 1/6\ H_2O$ | 54.53 54.80 | 3.59 3.80 | 11.22 10.95 | 17.12 16.74 | |

TABLE 2-continued

| Ex No. | Compd. No. | $R^1$ | Amount of (Ia) (mg) (mmol) | Yield of (Ic) (mg) (Yield: %) | M.P. (°C.) | Molecular Formula | Elementary Analysis (%) Up: Calcd. Down: Found | | | | |
|---|---|---|---|---|---|---|---|---|---|---|---|
| | | | | | | | C | H | N | S | F |
| 10 | Ic-5 | $CF_3$ | 369.9 (.¼ $H_2O$) (1.00) | 324.8 (85.2) | 176.0–176.5 (d) | $C_{16}H_{10}N_3OF_3S_2$ | 50.39 50.35 | 2.64 2.89 | 11.02 10.95 | 16.81 16.99 | 14.94 15.19 |

EXAMPLE 11

Synthesis of 1-ethoxycarbonyl-2-[(thieno[2,3-c]pyridin-7-yl)methylthio]benzimidazole (Ib-1)

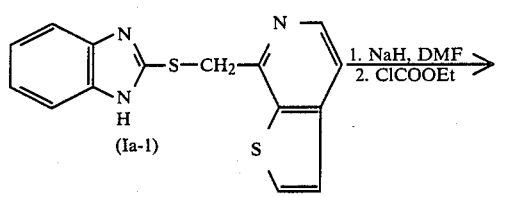

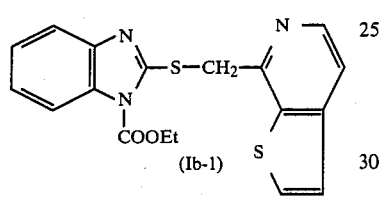

To 44.0 mg (1.10 mmol) of 60% NaH were added 7 ml of dry DMF and 299.2 mg (1.00 mmol) of 2-[(thieno[2, 3-c]pyridin-7-yl)methylthio]benzimidazole. 1/10 $H_2O$ (Ia-1). After stirring for 10 min. at room temperature, the solution was added with 130.2 mg (1.20 mmol) of ClCOOEt and stirred for 30 minutes at room temperature. DMF was evaporated under reduced pressure. Water was added to the residue, and the solution was extracted with $CH_2Cl_2$. After drying over anhydrous sodium sulfate, the solvent was evaporated under reduced pressure, whereby 381.0 mg of pale greenish yellow cyrstals were obtained. After being subjected to silica gel column chromatography, the crystals were dispersed with 2 ml of ether, followed by filtration and washed with ether, whereby 335.7 mg (Yield : 90.9%) of the objective compound, 1-ethoxycarbonyl-2-[(thieno[2, 3-c]pyridin-7-yl)methylthio]-benzimidazole (Ib-1) was obtained as crystals.

Melting point : 131.0 - 132.0° C.

Anal. Calcd. (%) for $C_{18}H_{15}N_3O_2S$ :
C, 58,82; H, 4.09; N, 11.37; S, 17.36.

Found (%) :C, 58.36; H, 4.01; N, 11.22; S, 17.33.

EXAMPLES 12–13

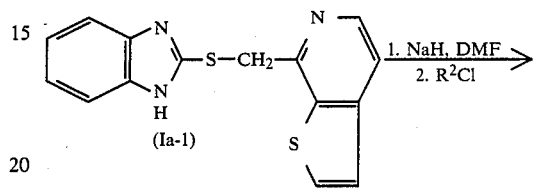

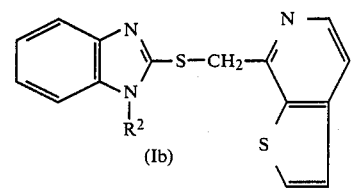

(wherein $R^2$ has the same meaning as defined above).

The reactions were performed under the conditions shown in Table 3 as in Example 11, whereby the objective compounds (Ib) were obtained.

TABLE 3

| Ex No. | Compd. No. | $R^2$ | Amount of (Ia) (g) (mmol) | Yield of (Ib) (g) (Yield %) | M.P. (°C.) | Molecular Formula | Elementary Analysis (%) Up: Calcd. Down: Found | | | |
|---|---|---|---|---|---|---|---|---|---|---|
| | | | | | | | C | H | N | S |
| 12 | Ib-2 | —COO—⌬ | 269.3 (.1/10 $H_2O$) (0.900) | 309.4 (82.3) | 157.0–159.0 (d) | $C_{22}H_{15}N_3O_2S$ | 63.29 63.29 | 3.62 3.72 | 10.06 9.92 | 15.36 15.10 |
| 13 | Ib-3 | —$CH_2OCO$—t-Bu | 269.3 (.1/10 $H_2O$) (0.900) | 288.6 (77.9) | 121.5–122.5 | $C_{21}H_{21}N_3O_2S_2$ | 61.29 61.22 | 5.14 5.17 | 10.21 10.21 | 15.58 15.45 |

EXAMPLE 14

Synthesis of 1-hydroxymethyl-2-[(thieno[2, 3-c]pyridin-7-yl)methylthio]benzimidazole (Ib-4)

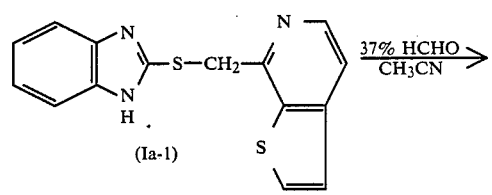

-continued

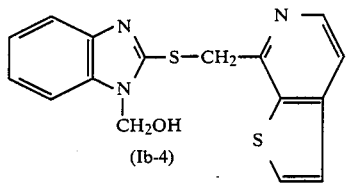

To 478.7 mg (1.60 mmol) of 2-[(thieno[2, 3-c]pyridin-7-yl)methylthio]benzimidazole. 1/10 H₂O (Ia-1) were added 8 ml of CH₃CN and 324.6 mg (4.00 mmol) of 37% aqueous solution of HCHO, and the mixture was stirred for 15 minutes at 70° C. After evaporation the solvent under reduced pressure, the residual crystals were washed with ether, whereby 420.9 mg (Yield : 80.3%) of the objective compound (Ib-4), 1-hydroxymethyl-2-[(thieno[2, 3-c]pyridin-7-yl)methylthio]benzimidazole was obtained as crystals.

IR: (Nujol) 1060, 765, 1340 cm⁻¹

NMR:δ (d₆-DMSO) 5.03 (s, 2H); 5.48 (d, 2H); 6.73 (t, 1J)

EXAMPLE 15

Snythesis of 1-acetyloxymethyl-2-[(thieno[2, 3-c]pyridin-7-yl)methylthio]benzimidazole (Ib-5)

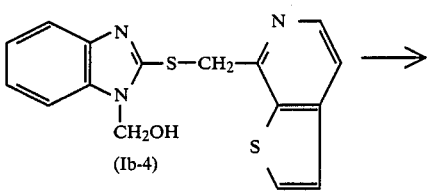

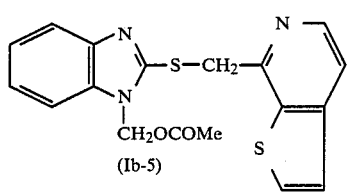

To 523.9 mg (1.60 mmol) of 1-hydroxymethyl-2-[(thieno[2, 3-c]pyridin-7-yl)methylthio]benzimidazole (Ib-4) were added 10 ml of pyridine, 2.61 g (25.6 mmol) of acetic anhydride and 15.6 mg (0.128 mmol) of 4-dimethylamiopyridine, and the mixture was stirred for 1 hr. at room temperature. Then, the mixture was poured into 100 ml of iced water, and the solution was extracted with CH₂Cl₂. The CH₂Cl₂ layer, after being washed with water, was dried over anhydrous sodium sulfate, and the solvent was evaporated under reduced pressure, whereby 0.60 g of brown liquid was obtained. After being subjected to silica gel column chromatography, the crystals were dispersed with 2 ml of a mixture of 50% ether - cyclohexane, followed by filtration and washed with 50% ether - cyclohexane, whereby 358.1 mg (Yield : 60.2%) of the objective compound (Ib-5), 1-acetyloxymethyl-2-[(thieno[2, 3-c]pyridin-7-yl)methylthio]benzimidazole was obtained as crystals.

Melting point : 114.5°–116.0° C.

Anal. Calcd. (%) for C₁₈H₁₅N₃O₂S₂1/8 H₂O :
C, 58.16; H, 4.14; N, 11.30; S, 17.25.

Found (%) : C, 58.17; H, 4.18; N, 11.19; S, 17.40.

EXAMPLE 16

Synthesis of 1-butyryloxymethyl-2-[(thieno[2, 3-c]pyridin-7yl)methylthio]benzimidazole (Ib-6)

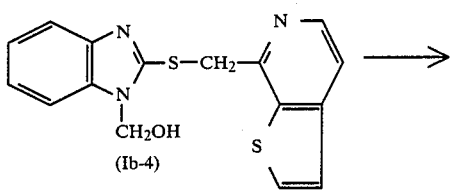

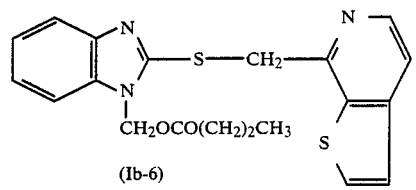

To 3.27 g (10.0 mmol) of the crystals (Ib-4) obtained by the reaction as in Example 14 were added 50 ml of pyridine, 7.91 g (50.0 mmol) of n-butyric anhydride and 97.7 mg (0.800 mmol) of 4-dimethylaminopyridine, and the mixture was stirred for 4 hr. at room temperature. Then, the mixture was poured into 500 ml of water, and the solution was extracted with AcOEt. After being washed with saturated aqueous NaHCO₃ and water, the AcOEt layer was dried over anhydrous sodium sulfate. The solvent was evaporated under reduced pressure, whereby 4.39 g of brown viscous liquid was obtained. After silica gel column chromatography, the crysrals were dispersed with 15 ml ofo cyclohexane, followed by filtration and washed with cyclohexane, whereby 2.70 g (Yield : 67.9%) of the objective compound (Ib-6), 1-butyryloxymethyl-2-[(thieno[2, 3-c]pyridin-7-yl)methylthio]benzimidazole was obtained as crystals.

Melting point : 78.5°–80.0° C.

Anal. Calcd. (%) for C₂₀H₁₉N₃O₂S₂ :
C, 60.43; H, 4.82; N, 10.57; S, 16.13.

Found (%) : C, 60.28; H, 4,84; N, 10.53; S, 15.91.

EXAMPLES 17–20

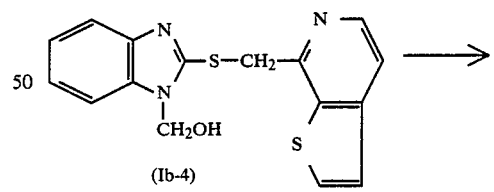

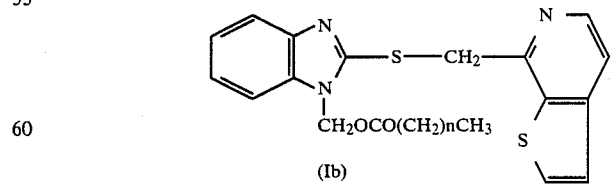

(wherein n is an integer of 1–5)

The reactions were performed under the conditions shown in Table 4 as in Example 16, whereby the objective compounds (Ic) were obtained. In each case, amount of Ib-4 is 523.9 g (1.60 mmol) and those of pyridine and 4-dimethylaminopyridine are 10 ml and 15.6 mg (0.128 mmol), respectively.

TABLE 4

| Ex No. | Compd. No. | n | Amount of carboxylic anhydride (g) (mmol) | Yield of (Ib) (mg) (Yield: %) | M.P. (°C.) | Molecular Formula | Elementary Analysis (%) Up: Calcd. Down: Found | | | |
|---|---|---|---|---|---|---|---|---|---|---|
| | | | | | | | C | H | N | S |
| 17 | Ib-7 | 1 | 1.04 (8.00) | 416.8 (67.6) | 98.0–99.0 | $C_{19}H_{17}N_3O_2S_2 \cdot 1/10\ H_2O$ | 59.23 59.22 | 4.50 4.47 | 10.91 10.76 | 16.64 16.49 |
| 18 | Ib-8 | 3 | 1.49 (8.00) | 374.7 (56.9) | 79.0–80.5 | $C_{21}H_{21}N_3O_2S_2$ | 61.29 61.33 | 5.14 5.36 | 10.21 10.25 | 15.58 15.46 |
| 19 | Ib-9 | 4 | 1.71 (8.00) | 365.8 (53.5) | 68.0–70.0 | $C_{22}H_{23}N_3O_2S_2 \cdot 1/10\ H_2O$ | 61.83 61.95 | 5.47 5.76 | 9.87 9.92 | 15.00 14.93 |
| 20 | Ib-10 | 5 | 1.94 (8.00) | 343.8 (48.9) | 84.5–85.5 | $C_{23}H_{25}N_3O_2S_2$ | 62.84 62.89 | 5.73 5.95 | 9.56 9.42 | 14.59 14.57 |

EXAMPLE 21

Synthesis of 1-ethoxycarbonyloxymethyl-2-[(thieno[2,3-c]pyridin-7-yl)methylthio]benzimidazole (Ib-11)

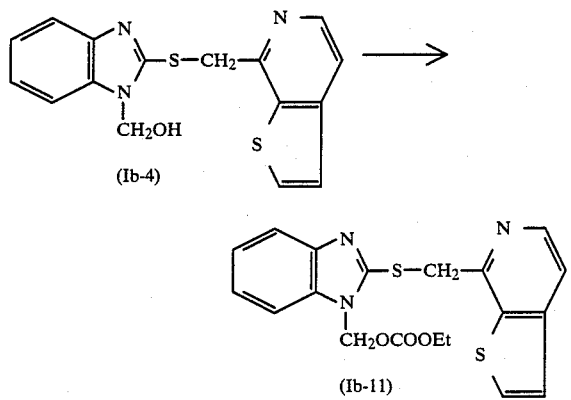

To 523.9 g (1.60 mmol) of the crystals (Ib-4) obtained by the reaction as in Example 14 were added 8 ml of pyridine and 208.4 mg (1.92 mmol) of ClCOOEt, and the mixture was stirred for 5 hr. at room temperature. After evaporating pyridine under reduced pressure, the residue was treated with water and the solution was extracted with AcOEt. The AcOEt layer was washed with water. After drying over anhydrous sodium sulfate, the solvent was evaporated under reduced pressure, whereby 624.7 mg of brown viscous liquid was obtained. After silica gel column chromatography, the crystals were dispersed with 2.5 ml of ether, followed by filtration and washed with ether, whereby 183.8 mg (Yield : 28.8%) of the objective compound (Ib-11), 1-ethoxycarbonyloxymethyl-2-[(thieno[2, 3-c]pyridin-7-yl)methylthio]benzimidazole was obtained as crystals.

Melting point: 90.0°–92.0° C.
Anal. Calcd. (%) for $C_{19}H_{17}N_3O_3S_2$:
C, 57.13; H, 4.29; N, 10.52; S, 16.05.
Found (%) : C, 57.20; H, 4.29; N, 10.45; S, 16.13.

EXAMPLE 22

Synthesis of 1-ethoxycarbonyl-2-[(thieno[2, 3-c]pyridin-7-yl)methylsulfinyl]benzimidazole (Ic-6)

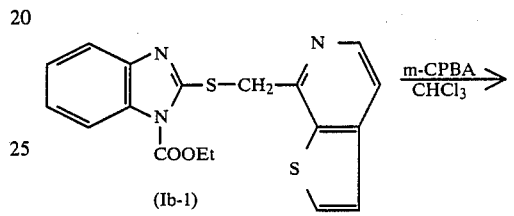

To a solution of 258.6 mg (0.700 mmol) of 1-ethoxycarbonyl2-[(thieno[2, 3-c]pyridin-7-yl)methylthio]benzimidazole (Ib-1) in 20 ml of $CHCl_3$ was added 151.0 mg (0.700 mmol) of 80% m-CPBA at -10 to -15 ° C., and the mixture was stirred for 1 hr. To the resultant solution were added 3 ml of saturated aqueous $NaHCO_3$ and 0.6 ml of 10 % aqueous sodium sulfite; and after cooling down to room temperature, the mixture was mixed with water and extracted with $CHCl_3$. After drying the $CHCl_3$ layer over anhydrous sodium sulfate, the solvent was evaporated under reduced pressure, whereby 355.3 mg of brown viscous liquid was obtained. After silica gel column chromatography, eluting with AcOEt, 123.8 mg (Yield : 45.2%) of the objective compound (Ic-6), 1-ethoxycarbonyl-2-[(thieno[2, 3-c]pyridin-7-yl)methylsulfinyl]benzimidazole was obtained as light brown amorphous. Recrystallizing from AcOEt gave crystals melting at 135.0°–136.0 ° C. (d).

Anal. Calcd. (%) for $C_{18}H_{15}N_3O_2S_2 \cdot 1/8\ H_2O$ :
C, 55.76; H, 3.96; N, 10.84; S, 16.54.
Found (%) : C, 55.76; H, 4.03, N, 10.74; S, 16.82.

EXAMPLES 23–25

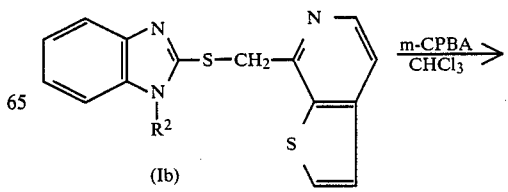

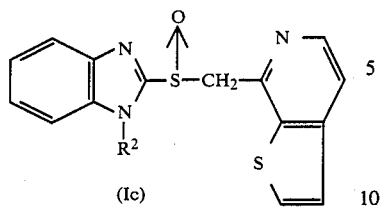

(wherein R¹ has the same meaning as defined above).

The reactions were performed under the conditions shown in Table 5, whereby the objective compounds (Ic) were obtained.

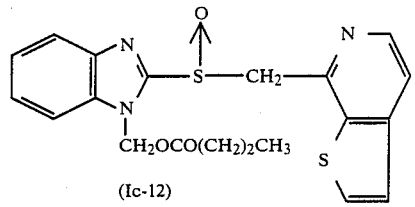

To a solution of 318.0 mg (0.800 mmol) of 1-butyryloxymethyl-2-[(thieno[2, 3-c]pyridin-7-yl)methylthio]benzimidazole (Ib-6) in 30 ml of CHCl₃ was added 224.3 mg (1.04 mmol) of 80% m-CPBA at −10° to −15° C., and the mixture was stirred for 1 hr. To the

TABLE 5

| Ex. No. | Compd. No. | R² | Amount Ib (mg) (mmol) | Reaction Time (hr) | Reaction Temp. (°C.) | Reaction Solvent | Yield of Ic (mg) (Yield: %) |
|---|---|---|---|---|---|---|---|
| 23 | Ic-7 | —COO—⟨phenyl⟩ | 288.2 (0.690) | 1 | −10– −15 | CHCl₃ | 112.0* (35.9) |
| 24 | Ic-8 | —CH₂OCO—t-Bu | 288.1 (0.700) | 1 1 | −10– −15 | CHCl₃ | 114.8 (38.1) |
| 25 | Ic-9 | —CH₂OCOMe | 297.4 (.1/8 H₂O) (0.800) | 1 | −10– −15 | CHCl₃ | 158.0 (50.9) |
| 26 | Ic-10 | —CH₂SMe (with C=O) | 360.0 (0.970) | 0.5 | −10 | CHCl₃ MeOH (10:1 v/v) | 110.0 28.8) |
| 27 | Ic-11 | —CH₂OCOCH₂Cl | 370.0 (0.92) | 0.5 | −10 | CHCl₃ | 140.0 (36.4) |

| Ex. No. | M.P. (°C.) | Molecular Formula | Elementary Analysis (%) Up: Calcd. Down: Found | | | |
|---|---|---|---|---|---|---|
| | | | C | H | N | S |
| 23 | 134.5– 135.5 (d) | C₂₂H₁₅N₃O₂S₂.H₂O | 58.52 58.46 | 3.79 3.54 | 9.31 9.22 | 14.20 13.96 |
| 24 | 135.0– 136.0 (d) | C₂₁H₂₁N₃O₃S. 1/7 H₂O | 58.64 58.63 | 4.99 5.04 | 9.77 9.67 | 14.91 14.58 |
| 25 | 134.4– 135.0 (d) | C₁₈H₁₅N₃O₃S₂. 1/7 H₂O | 55.72 55.74 | 3.97 3.96 | 10.83 10.82 | 16.52 16.23 |
| 26 | 139.0– 142.0 (d) | C₁₇H₁₅ N₃S₃O₂. 0.38 H₂O | 51.52 51.81 | 4.01 4.04 | 10.60 10.52 | 24.27 23.98 |
| 27 | 155– 157 (d) | C₁₈H₁₄N₃S₂ClO₃ | 51.49 51.41 | 3.36 3.28 | 10.01 9.82 | 15.27 15.06 Cl 8.44 Cl 8.69 |

*decomposed by chromatography on silica gel

EXAMPLE 28

Synthesis of 1-butyryloxymethyl-2-[(thieno[2, 3-c]pyridin-7-yl)methylsulfinyl]benzimidazole (Ic-12)

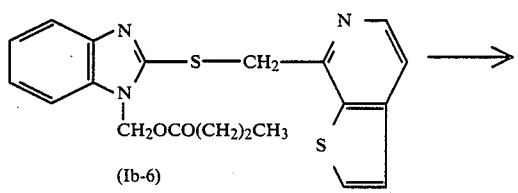

solution were added 3 ml of saturated aqueous NaHCO₃ and 0.6 ml of 10% aqueous sodium sulfite. After bringing back to room temperature, the solution was mixed with water and extracted with CHCl₃. After drying CHCl₃ layer over anhydrous sodium sulfate, the solvent was evaporated under reduced pressure, whereby brown viscous liquid was obtained. After silica gel column chromatography, the crystals were dispersed with ether, followed by filtration and washed with ether, whereby 169.8 mg (Yield : 51.3%) of the objective compound (Ic-12), 1-butyryloxymethyl-2-[(thieno[2, 3-c]pyridin7-yl)methylsulfinyl]benzimidazole was obtained as crystals.

Melting point : 118.0°–119.0° C. (d)
Anal. Calcd. (%) for C₂₀H₁₉N₃O₃S₂:
C, 58.09; H, 4.63; N, 10.16; S, 15.51.

Found (%): C, 58.06; H, 4.70; N, 10.05; S, 15.35.

EXAMPLES 29-32

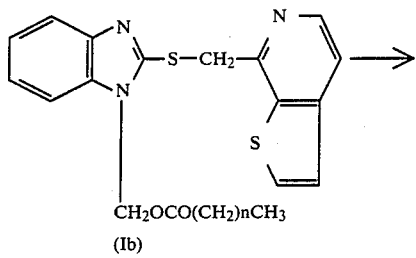
(Ib)

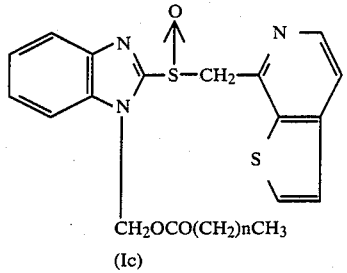
(Ic)

(wherein n is an integer).

The reactions were performed under the conditions shown in Table 6 as in Example 28, whereby the objective compounds (Ic) were obtained.

-continued

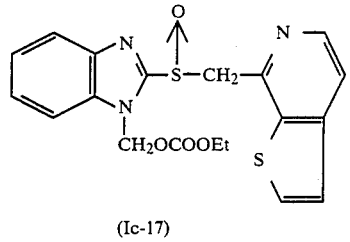
(Ic-17)

To a solution of 279.6 mg (0.700 mmol) of 1-ethoxycarbonyloxymethyl-2-[(thieno[2, 3-c]pyridin-7-yl)methylthio]benzimidazole (Ib-11) in 30 ml of CHCl, was mixed with 226.5 mg (1.05 mmol) of 80% m-CPBA at −10° to −15° C., and stirred for 1 hr. The mixture was treated with 3 ml of saturated aqueous NaHCO3 and 0.6 ml of 10% aqueous sodium sulfite, and after bringing back to room temperature, the solution was mixed with water and extracted with CHCl3. After drying CHCl3 layer over anhydrous sodium sulfate, the solvent was evaporated under reduced pressure, whereby brown viscous liquid was obtained. After silica gel column chromatography, the crystals were dispersed with 3 ml of ether, followed by filtration and washed with ether, whereby 158.0 mg (Yield : 54.3%) of the objective compound (Ic-17), 1-ethoxycarbonyloxymethyl-2-[(thieno[2, 3-c]pyridin-7-yl]methylsulfinyl]benzimidazole was obtained as crystals.

TABLE 6

| | Ib | | | Ic | | | | | | |
|---|---|---|---|---|---|---|---|---|---|---|
| | | Amount of Ib | | | Amount of Ic | | | | Elementary Analysis (%) Up: Calcd. Down: Found | | | |
| Ex No. | Compd. No. | (mg) (mmol) | n | Compd. No. | (mg) (Yield: %) | M.P. (°C.) | Molecular Formula | C | H | N | S |
| 29 | Ib-7 | 308.2 (.1/10 H2O) (0.800) | 1 | Ic-13 | 155.3 (48.6) | 127.0–128.5 (d) | $C_{19}H_{17}N_3O_3S_2$ | 57.13 56.96 | 4.29 4.24 | 10.52 10.42 | 16.05 15.96 |
| 30 | Ib-8 | 308.7 (0.750) | 3 | Ic-14 | 182.1 (56.8) | 84.0–85.0 | $C_{21}H_{21}N_3O_3S_2$ | 59.00 58.86 | 4.95 5.07 | 9.83 9.74 | 15.02 15.12 |
| 31 | Ib-9 | 307.7 (.1/10 H2O) (0.720) | 4 | Ic-15 | 182.0 (57.2) | 98.5–99.5 | $C_{22}H_{23}N_3O_3S_2$ | 59.84 59.90 | 5.25 5.38 | 9.52 9.51 | 14.52 14.27 |
| 32 | Ib-10 | 307.7 (0.700) | 5 | Ic-16 | 162.3 (50.9) | 99.0–100.0 | $C_{23}H_{25}N_3O_3S_2$ | 60.64 60.42 | 5.53 5.57 | 9.22 9.08 | 14.07 14.27 |

Melting point : 141.0°–143.0° C. (d)
Anal. Calcd. (%) for $C_{19}H_{17}N_3O_4S_2$:
C, 54.93; H, 4.12; N, 10.11; S, 15.43.
Found (%) : C, 54.82; H, 4.20; N, 9.95; S, 15.30.

EXAMPLE 33

Synthesis of 1-ethoxycarbonyloxymethyl-2-[(thieno[2, 3-c]pyridin-7-yl)methylsulfinyl]benzimidazole (Ic-17)

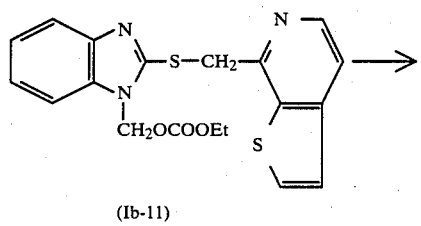
(Ib-11)

EXAMPLE 34

Synthesis of 2-[(thieno[3, 2-c]pyridin-4-yl)methylthio]benzimidazole (Ia')

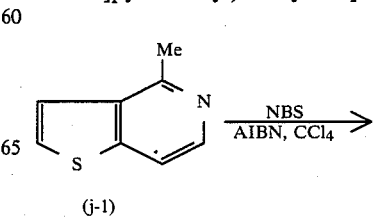
(j-1)

-continued

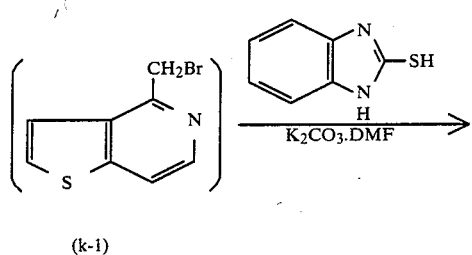

(k-1)

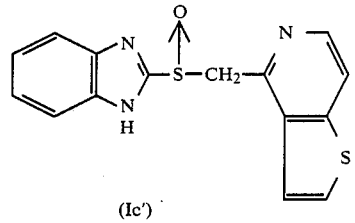

(Ic')

To a solution of 278.6 mg (0.900 mmol) of 2-[(thieno[3, 2-c]pyridin-4-yl)methylthio]benzimidazole.2/3 H₂O (Ia') in 20 ml of CHCl₃ and 1 ml of MeOH was added 194.1 mg (0.900 mmol) of 80% mCPBA at −10° to −15° C. and stirred for 30 minutes. To the mixture were added 2.5 ml of saturated aqueous NaHCO₃ and 0.5 ml of 10 % aqueous sodium sulfite. After bringing back to room temperature, water was added thereto, and the solution was extracted with CHCl₃. After drying CHCl₃ layer over anhydrous sodium sulfate, the solvent was evaporated under reduced pressure and washed with ether, whereby 274.6 mg (Yield : 92.5%) of the objective compound (Ic'), 2-[(thieno[3, 2-c]pyridin-4-yl)methylsulfinyl]benzimidazole was obtained as crystals.

Melting point : 186.0°–187.5° C. (d)
Anal. Calcd. (%) for $C_{15}H_{11}N_3OS_2 \cdot 1/5$ H₂O :
C, 56.84; H, 3.62; N, 13.26; S, 20.23.
Found (%) : C, 56.99; H, 3.54; N, 13.06; S, 19.86.

(Ia')

To 1.343 g (9.00 mmol) of 4-methylthieno[3, 2-c]pyridine j-1 were added 55 ml of CCl₄, 2.56 g (14.4 mmol) of N-bromosuccinimide and 23.6 mg (0.144 mmol) of 2,2′-azobisisobutyronitrile, and the mixture was refluxed for 16 hr. After being cooled down to room temperature, the mixture was subjected to silica gel column chromatography for purification, whereby a solution of 4-bromoethylthieno[3, 2-c]pyridine (k-1) was obtained. K-1 is stable in solution, but it decomposed within solvent.

NMR: δ (CDCl₃) 4.89 (s, 2H); 7.61 (s, 2H); 7.77 (d, 1H); 8.41 (d, 1H)

The solution ((k-1) obtained was concentrated to about 20 ml. To the solution were added 675.9 mg (4.50 mmol) of 2-mercaptobenzimimdazole, 3.11 g (22.5 mmol) of K₂CO₃ and 30 ml of dry DMF, and the mixture was stirred for 21 hr. at room temperature. After evaporating DMF under reduced pressure, water was added to the residue and the solution was extracted with CH₂Cl₂. After separating the insoluble material by filtration, CH₂Cl₂ layer was dried over anhydrous sodium sulfate and concentrated under reduced pressure, whereby 0.66 g of a crude produce was obtained. The produce was subjected to silica gel column chromatography and washed with ether, whereby 442.0 mg (Yield : 15.9%) of the objective compound (Ia'), 2-[(thieno[3, 2-c]pyridin-4-yl)methylthio]benzimidazole was obtained as crystals.

Melting point 205°–208° C. (d)
Anal. Calcd. (%) for $C_{15}H_{11}N_3S \cdot 2/3$ H₂O :
C, 58.23; H, 4.02; N, 13.58; S, 20.72.
Found (%) : C, 58.23; H, 3.93; N, 13.60; S, 20.63.

EXAMPLE 35

Synthesis of 2-[(thieno[3, 2-c]pyridin-4-yl)methylsulfinyl]benzimidazole (Ic')

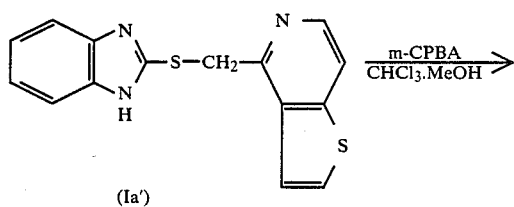

(Ia')

EXAMPLE 36

Synthesis of 2-[(bromothieno[2, 3-c]pyridin-7-yl)methylsulfinyl]benzimidazole (Ic-18)

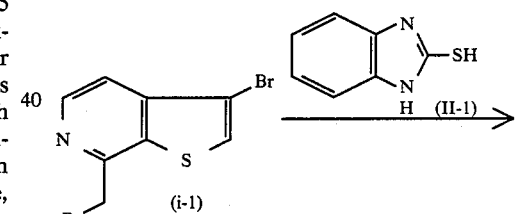

(i-1)

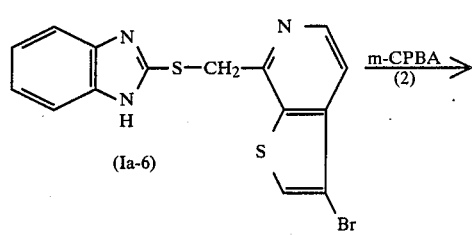

(Ia-6)

(Ic-18)

(1) A mixture of 158 mg (0.515 mmol) of 3-bromo-7-bromomethylthieno[2, 3-c]pyridine (i-1), 85 mg (1.1 equivalents) of 2-mercaptobenzimidazole, 284 mg (4 equivalents) of anhydrous K₂CO₃ and 4 ml of anhydrous DMF was stirred for 1 hr. at room temperature. Water was added to the mixture, and crystals separated out. The crystals collected by filtration were dried, whereby 183 mg (94.5%) of 2-[(3-bromothieno[2, 3-c]pyridin-7-yl)methylthio]benzimidazole (Ia-6) was obtained as an objective compound.

NMR: $\delta$d⁶-DMSO CDCl₃ 5.00 (s, 2H); 7.03–7.20 (m, 2H), 7.40–7.53 (m, 2H) 7.63, 8.55 (ABq, 2H), 8.06 (s, 1H)

Melting point : 172°–174° C. (recrystallized from CHCl₃ - MeOH: containing 1 mole of MeOH)

Anal. Calcd. (%) for $C_{16}H_{14}N_3S_2BrO \cdot MeOH$: C, 47.06; H, 3.46; N, 10.29; S, 15.70; Br, 19.57.

Found (%) : C, 46.80; H, 3.40; N, 10.17; S, 15.83; Br, 19.92.

(2) To a solution of 90 mg (0.239 mmol) of 2-[(3-bromothieno[2,3-c]pyridin-7-yl)methylthio]benzimidazole (Ia-6) in 4 ml of CHCl₃ and 1 ml of MeOH was added 52 mg (1.0 equivalent) of 80% m-CPBA at −20° C., and the mixture was stirred for 1 hr. at −20° C. When 10% aqueous sodium sulfite and saturated aqueous NaHCO₃ were added to the mixture, crystals separated out and collected by filtration. The extract of the mother liquid with CHCl₃ was combined with the crystals and subjected to silica gel column chromatography for purification, whereby 61 mg (Yield : 65.0%) of 2-[(3-bromothieno[2, 3-c]pyridin-7-yl)methylsulfinyl]benzimidazole (Ic-18) was obtained as an objective compound.

NMR: $\delta$d⁶-DMSO CDCl₃ 4.93, 5.10 (ABq, J = 15 Hz, 2H); 7.20–7.40 (m, 2H); 7.60 -7.80 (m, 3H); 8.16 (s, 1H); 8.60 (d, j=6Hz, 1H)

Melting point: 178°–185° C. (d) (recrystallized from CHCl₃-MeOH)

Anal. Calcd. (%) for $C_{15}H_{10}N_3OS_2Br$ : C, 45.93; H, 2.57; N, 10.71; S, 16.35.

Found (%) : C, 45.60, H, 2.71; N, 10.46; S, 15.99.

EXAMPLES 37–39

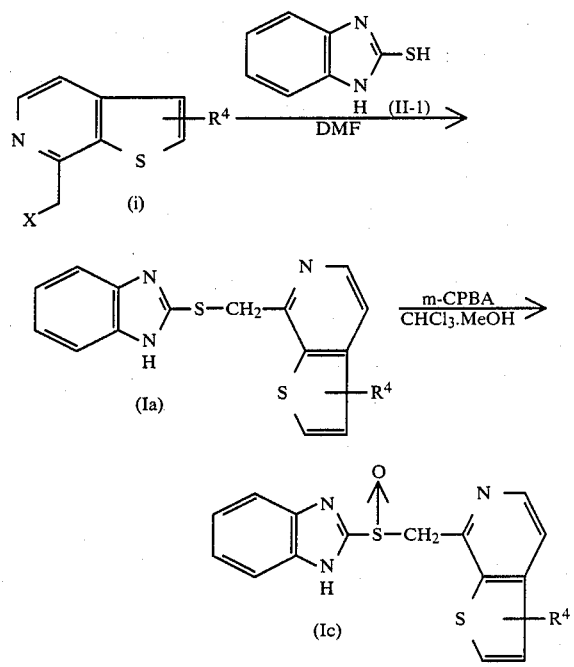

(wherein R⁴ and X have the same meaning as defined above)

The reactions were performed under the conditions shown in Tables 7 and 8 as in Example 34, whereby the objective compounds (Ia) and (Ic) were obtained.

TABLE 7

| Ex. No. | Compd. No. | R⁴ | X | Amount of i (mg) (mmol) | Amount of II-1 (mg) (equivalent) | Amount of K₂CO₃ (mg) (equivalent) | Amount of DMF (ml) | Reaction Time (hr) | Reaction Temp. (° C.) | Yield of Ia (mg) Yield: % | NMR or IR |
|---|---|---|---|---|---|---|---|---|---|---|---|
| 37 | Ia-7 | 2-Br | Br | 100 (0.326) | 54 (1.1) | 180 (4.0) | 2.5 | 1 | Room Temp. | 97 (79.1) | NMR: $\delta^{CDCl_3}_{d6-DMSO}$ 4.90 (s, 2H); 7.05–7.20 (m, 2H); 7.40–7.50 (m, 2H); 7.63, 8.36 (ABq, J = 6Hz, 2H); 8.05 (s, 1H) |
| 38 | Ia-8 | 3-CN | Cl | 144 (0.69) | 110 (1.05) | 380 (4.0) | 4 | 2.5 | Room Temp. | 153 (76.2) | NMR: $\delta^{CDCl_3}_{d6-DMSO}$ 5.06 (s, 2H), 7.00–7.20 (m, 2H) 7.30–7.60 (m, 2H); 7.81, 8.60 (ABq, J = 6Hz, 2H); 9.10 (s, 1H) |
| 39 | Ia-9 | 3-CONH₂ | Cl | 220 (0.972) | 153 (1.05) | 537 (4.0) | 6 | 2 | Room Temp. | 218 (65.9) | NMR: $\delta^{CDCl_3}_{d6-DMSO}$ 5.00 (s, 2H); 7.05–7.25 (m, 2H); 7.40–7.60 (m, 2H); 8.42, 8.50 (ABq, J = 5Hz, 2H); 8.70 (s, 1H) IR: $\nu^{Nujol}_{max}$ 3400, 3150 1660 (cm⁻¹) |

TABLE 8

| Compd. No. | $R^3$ | Amount of Ia (mg) (mmol) | Amount of CHCl$_3$ (ml) | Amount of MeOH (ml) | Amount of m-CPBA (mg) (equivalent) | Reaction Time (hr) | Reaction Temp. (°C.) | M.P. (°C.) | Yield of Ic (mg) (Yield: %) | NMR or Elementary Analysis |
|---|---|---|---|---|---|---|---|---|---|---|
| Ic-19 | 2-Br | 90 (0.239) | 6 | 1 | 57 (1.1) | 1.25 | −20 | —* | 89 (94.9) | NMR: $\delta^{CDCl_3}_{d6-DMSO}$4.83, 5.00 (ABq, J = 15Hz, 2H); 7.30–7.43 (m, 2H); 7.50–7.80 (m, 3H); 8.43 (d, J = 6Hz, 1H) Anal. Calcd. (%) for C$_{15}$H$_{10}$N$_3$OS$_2$Br: C, 45.93; H, 2.57; N, 10.71; S, 16.35 Found (%): C, 45.72; H, 2.79; N, 10.74; S, 16.16 |
| Ic-20 | 3-CN | 106 (0.329) | 30 | 10 | 83 (1.2) | 1 | −10 | 198–202 (d) | 80 (64.8) | NMR: $\delta^{CDCl_3}_{d6-DMSO}$5.00, 5.15 (ABq, J = 14Hz, 2H); 7.20–7.40 (m, 2H); 7.53–7.73 (m, 2H); 7.86, 8.12 (ABq, J = 6Hz, 2H); 9.10 (s, 1H) Anal. Calcd. (%) for C$_{16}$H$_{10}$ON$_4$OS$_2$·0.17 H$_2$O: C, 56.28; H, 3.05; N, 16.41; S, 18.78 Found (%): C, 56.49; H, 3.07; N, 16.16; S, 18.74 |
| Ic-21 | 3-CONH$_2$ | 150 (0.441) | 20 | 10 | 115 (1.2) | 1.5 | −10 | 214–216 (d) | 90 (57.2) | NMR: $\delta^{CDCl_3}_{d6-DMSO}$4.92, 5.07 (ABq, J = 13Hz, 2H); 7.20–7.40 (m, 2H); 7.56–7.73 (m, 2H); 8.43, 8.50 (ABq, J = 6Hz, 2H); 8.70 (s, 1H) Anal. Calcd. (%) for C$_{16}$H$_{12}$N$_4$O$_2$S$_2$·0.96 H$_2$O: C, 51.42; H, 3.75; N, 14.99; S, 17.16 Found (%): C, 51.64; H, 3.61; N, 14.88; S, 17.04 |

*The compound does not show definite melting point. It turns black gradually, and completely decomposes around 300° C.

EXAMPLE 40

Synthesis of 2-[(3-methoxycarbonylthieno[2,3-c]pyridin-7-yl)methylsulfinyl]benzimidazole (Ib-22)

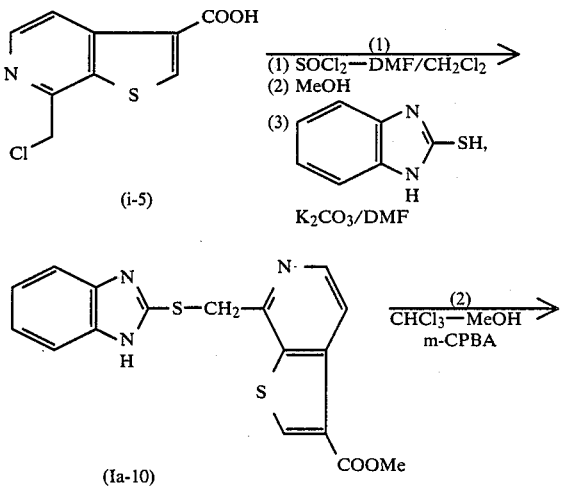

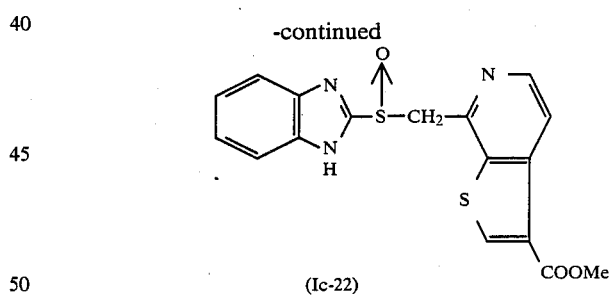

(1) To a mixture of 110 mg (0.483 mmol) of 3-carboxy-7-chloromethylthieno[2, 3-c]pyridine (i-5), 2 ml of dichloromethane and 2 drops of anhydrous DMF was added 0.1 ml (2.8 equivalents) of thionyl chloride, and the mixture was stirred for 2.5 hr. at room temperature. Then the solution was treated with 3 ml of anhydrous methanol, stirred for 30 min. at room temperature and refluxed for 2 min. After concentration under reduced pressure, 2 ml of anhydrous DMF, 88 mg (1.2 equivalents) of 2-mercaptobenzimidazole and 536 mg (8 quivalents) of anhydrous K$_2$CO$_3$ were added to the solution and the mixture was stirred for 4 hr. at room temperature. After concentration under reduced pressure, the mixture was extracted with ethyl acetate and subjected to silica gel column chromatography, eluting with CH$_2$Cl$_2$—ethyl acetate. From the eluate, 140 mg (Yield : 81.5%) of 2-[(3-methoxycarbonylthieno[2, 3- c]pyridin-7-yl)methylthio]benzimidazole (Ia-10) was obtained as a foamy product.

NMR: $\delta^{CDCl_3}$ 3.97 (s, 3H); 4.68 (s, 2H); 7.10–7.30 (m, 2H); 7.50–7.65 (m, 2H); 8.42, 8.62 (ABq, J=6Hz, 2H)

(2) To a solution of 140 mg (0.433 mmol) of 2-[(3-methoxycarbonylthieno[2, 3-c]pyridin-7-yl)methylthio]benzimidazole (Ia-10) in 6 ml of CHCl₃ and 2 ml of MeOH was added 94 mg (1.1 equivalents) of 80% m-CPBA in the ice-water bath of −10° C., and the mixture was allowed to react for 1 hr. at −10° C. The solution was treated with 10 % aqueous sodium sulfite and saturated aqueous NaHCO₃ and extracted with CH₂Cl₂. The extract was subjected to silica gel column chromatography, eluting with CH₂Cl₂—MeOH, and the eluate gave 122 mg (Yield : 75.8%) of 2-[(3-carbomethoxythieno[2, 3-c]pyridin-7-yl)methylsulfinylbenzimidazole (Ic-22) as a foamy product.

Melting point: 190°–197° C. (d) (recrystallized from ethyl acetate—MeOH)

NMR: $\delta^{CDCl_3}$ 3.93 (s, 3H); 4.87, 5.03 (ABq, J=14Hz, 2H); 7.13–7.40 (m, 2H); 7.50–7.75 (m, 2H); 8.32, 8.53 (ABq, J=6Hz, 2H); 8.36 (s, 1H).

Anal. Calcd. (%) foro $C_{17}H_{13}N_3O_3S_2$: C, 54.97; H, 3.53; N, 11.31; S, 17.26.

Found (%) : C, 54.60, H, 3.56; N, 11.12; S, 17.02.

EXAMPLE 41

Synthesis of 2-[(3-methylthieno[2, 3-c]pyridin-7-yl)methylsulfinyl]-1-(pivaloyloxymethyl)-benzimidazole (Ic-24)

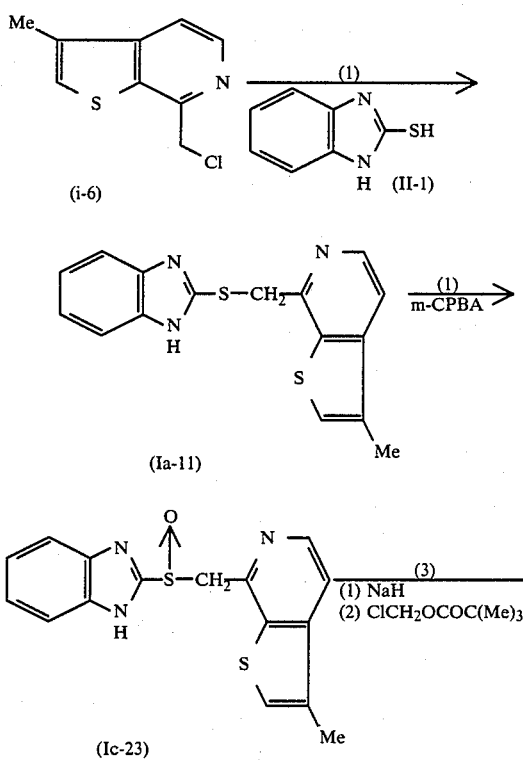

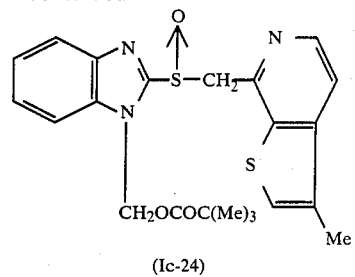

(1) To a suspension of 1.82 g of 2-mercaptobenzimidazole and 6.7 g of K₂CO₃ in 35 ml of DMF was added 2.4 g of 7-chloromethyl-3-methylthieno[2, 3-c]pyridine, and the mixture was stirred for 2 hr. DMF was evaporated under reduced pressure, and CHCl₃ was added to the residue for extraction. The CHCl₃ layer was washed with water and dried. Then, CHCl₃ was removed by evaporation, and ether was added to he residue, whereby 3.41 g (Yield : 90.5%) of the objective product (Ia-11), 2-[(3-methylthieno[2, 3-c]pyridin-7-yl)methylthio]benzimidazole was obtained as crystals.

Melting point: 160°–162° C. (recrystallized from ethyl acetate)

Anal. Calcd. (%) for $C_{16}H_{13}N_3S_2$: C, 61.71; H, 4.21; N, 13.49; S, 20.59.

Found (%) : C, 62.00; H, 4.34; N, 13.43; S, 20.64.

(2) A solution of 2.34 g of Compound (Ia-11) in 60 ml of CHCl₃ was cooled to −10° C., and 1.62 g of 80% m-CPBA was added to the solution. The mixture was stirred for 25 min. at −5° C., and then neutralized with saturated aqueous NaHCO₃. After bringing back to room temperature, the CHCl₃ layer was dried, and CHCl₃ was removed by evaporation. The residue was subjected to silica gel column chromatography, eluting with ethyl acetate, and the fraction of the eluate gave 1.98 g (Yield : 80.5 %) of 2-[(3-methylthieno[2, 3-c]pyridin-7-yl)methylsulfinyl]benz-imidazole (Ic-23) as an objective compound.

Melting point: 186°–188° C. (recrystallized from ethanol)

Anal. Calcd. (%) for $C_{16}H_{13}N_3S_2O$ :
C, 58.69; H, 4.00; N, 12.83; S, 19.58.

Found (%) : C, 58.77; H, 4.02; N, 12.63; S, 19.62.

(3) To a solution of 1.3 g of Compound (Ic-23) in 40 ml of DMF was added 0.175 g of 60% NaH (oily substance), and the mixture was stirred for 15 min. Then, the mixture was mixed with 0.6 ml of chloromethyl pivalate and stirred for 6.5 hr. DMF was evaporated under reduced pressure, and the residue was extracted with CHCl₃, followed by washing with water and drying, and then CHCl₃ was removed by evaporation. The residue was subjected to silica gel column chromatography, eluting with ethyl acetate, and the fraction of the eluate gave 0.25 g (Yield : 14.3%) of 2-[(3-methylthieno[2, 3-c]pyridin-7-yl]methylsulfinyl]-1-pivaloyloxymethyl)benzimidazole (Ic-24) as an objective compound.

Melting point: 135°–137° C. (d) (recrystallized from ethyl acetate)

Anal. Calcd. (%) for $C_{22}H_{23}N_3S_2O_3$:
C, 59.84; H, 5.25; N, 9.52; S, 14.52.

Found (%) : C, 59.77; H, 5.16; N, 9.37; S, 14.31.

EXAMPLES 42-43

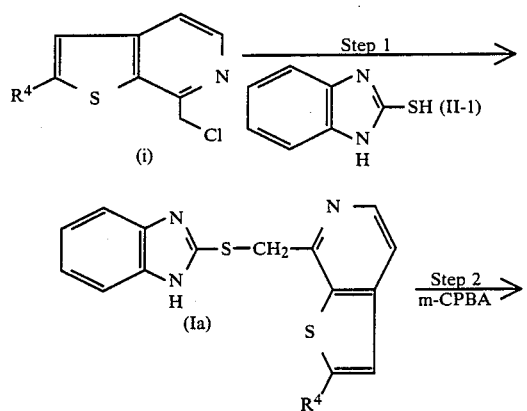

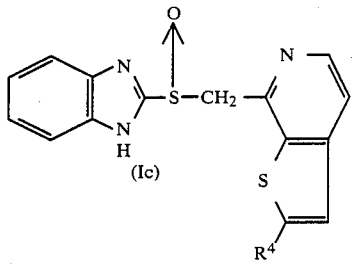

(wherein R⁴ has the same meaning as defined above).

The reaction was performed under the conditions shown in Table 9 and 10 as in Step 1 and Step 2 of Example 41, whereby the objective compounds (Ia) and (Ic) were obtained.

TABLE 9

| | | | | | | Step 1 | | | Elementary Analysis (%) Up: Calcd. Down: Found | | | | |
|---|---|---|---|---|---|---|---|---|---|---|---|---|---|
| Ex. No. | R⁴ | Amount of i (g) | Amount of 2-Mercapto-benzimida-zole (g) | Amount of K₂CO₃ (g) | Amount of DMF (ml) | Reaction Time (hr) | Yield of Ia (g) (Yield: %) | M.P. (°C.) | Molecular Formula (Appearance) | C | H | N | S | Compd. No. |
| 42 | Me | 1.85 | 1.4 | 5.2 | 30 | 2 | 2.39 (82.1) | 160-162 | $C_{16}H_{13}N_3S_2$ (Prism-shaped) | 61.71 61.84 | 4.21 4.23 | 13.49 13.25 | 20.59 20.46 | Ia-12 |
| 43 | Et | 0.76 | 0.54 | 1.98 | 13 | 2 | 0.92 (74.8) | 125-127 | $C_{17}H_{15}N_3S_2$ (Prism-shaped) | 62.74 62.73 | 4.65 4.61 | 12.91 12.75 | 19.70 19.63 | Ia-13 |

TABLE 10

| | | | | | Step 2 | | | | Elementary Analysis (%) Up: Calcd. Down: Found | | | | |
|---|---|---|---|---|---|---|---|---|---|---|---|---|---|
| Ex. No. | Amount of Ia (g) | Amount of CHCl₃ (ml) | Amount of 80% m-CPBA (g) | Reaction Time (min) | Reaction Solvent | Yield of Ib (g) (Yield: %) | M.P. (°C.) | Molecular Formula (Appearance) | C | H | N | S | Compd. No. |
| 42 | 0.934 | 50 | 0.68 | 20 | CHCl₃ | 0.97 (98.2) | 176-178 (d) | $C_{16}H_{13}N_3S_2O$ (Pillar-shaped) | 58.69 58.59 | 4.00 4.10 | 12.83 12.71 | 19.58 19.36 | Ic-25 |
| 43 | 0.81 | 40 | 0.56 | 20 | CHCl₃—MeOH (10:1 v/v) | 0.82 (96.5) | 158-160 (d) | $C_{17}H_{15}N_3S_2O$ (Needles) | 59.80 59.67 | 4.43 4.41 | 12.31 12.22 | 18.78 18.57 | Ic-26 |

EXAMPLE 44

Synthesis of 2-[(3-acetaminothieno[2,3-c]pyridin-7-yl)methylthio]benzimidazole (Ia-12)

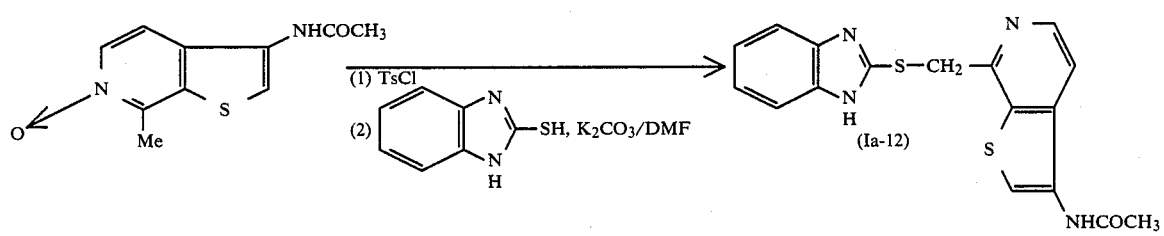

To a refluxing solution of 202 mg (0.909 mmol) of 3-acetamino7-methylthieno[2, 3-c]pyridine N-oxide in anhydrous benzene was added 258 mg (1.5 equivalents) of TsCl, and the mixture was continued to be refluxed for 4 hr. After concentration under reduced pressure, the solution was subjected to silica gel column chromatography (silica gel : 30 g), eluting with CH₂Cl₂: MeOH=20:1 v/v, whereby 3-acetamino-7-chloromethylthieno[2, 3-c]pyridine was separated. The produce was treated with 3 ml of anhydrous DMF, 136 mg (1 equivalent) of 2-mercaptobenzimidazole, and 502 mg (4 equivalents) of anhydrous K$_2$CO$_3$, and the mixture was stirred for 2.5 hr. at room temperature. After concentration under reduced pressure, the residue was extracted with ethyl acetate, and washed with water. The organic layer gave 237 mg of the crude crystals. The crystals were subjected to silica gel column chromatography (silica gel : 60 g), eluting with a solution of CH$_2$Cl$_2$ : MeOH=10:1 v/v, whereby 83 mg (Yield : 26.8%) of 2-[(3-acetaminothieno[2, 3-c]pyridin-7-yl]methylthio]benzimidazole (Ia-12) was obtained as an objective compound.

NMR: δC.D$_3$OD CDCl$_3$ 2.23 (s, 3H); 4.80 (s, 2H); 7.10–7.30 (m, 2H); 7.40–7.60 (m, 2H); 7.86, 8.43 (ABq, J=6Hz, 2H); 8.20 (s, 1H)

EXAMPLE 45

Synthesis of 2-[(3-acetaminothieno[2, 3-c]pyridin-7-yl)methylsulfinyl]benzimidazole (Ic-27)

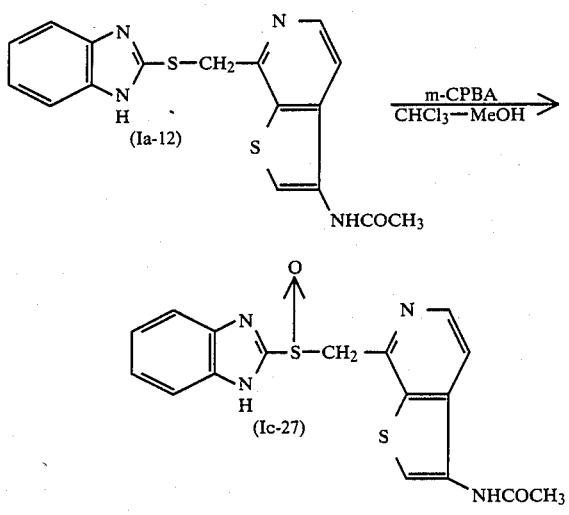

To a solution of 83 mg (0.244 mmol) of 2-[(3-acetaminothieno[2, 3-c]pyridin-7-yl)methylthio]benzimidazole (Ia-12) was dissolved in a mixture of 4 ml of CHCl$_3$ and 2 ml of MeOH. To the solution was added 53 mg (1 equivalent) of 80% m-CPBA at -10° C., and the mixture was stirred for 1.5 hr. at the same temperature. By adding an appropriate quantity each of 10% Na$_2$SO$_3$ and saturated aqueous NaHCO$_3$ to the solution, crystals separated out. The crystals were collected by filtration to give 72 mg of crude crystals. The crystals were recrystallized from a solution of CHCl$_3$ - MeOH, whereby 53 mg (Yield : 60.9%) of 2-[(3-acetaminothieno[2, 3-c]pyridin-7-yl)methylsulfinyl]benzimidazole (Ic-27) was obtained as an objective compound.

Melting point : 160 - 165° C. (d)

Anal. Calcd. (%) for C$_{17}$H$_{14}$N$_4$O$_2$S$_2$ 1.7 H$_2$O : C, 50.91; H, 4,37; N, 13.97; S, 15.99

Found (%) : C, 51.16; H, 4.34; N, 13.76; S, 15.80

NMR: ° C.D$_3$OD CDCl$_3$ 2.25 (s, 3H); 4.86, 5.03 (ABq, J=15Hz, 2H);

7.26 - 7.50 (m, 2H); 7.56, 7.80 (m, 2H);

7.92, 8.46 (ABq, J=6Hz, 2H); 8.20 (s, 1H). EXAMPLE 46

Synthesis of 1-(methylthiomethyl)-2-[(thieno[2, 3-c]pyridin-7yl)methylthio]benzimidazole (Ib-12)

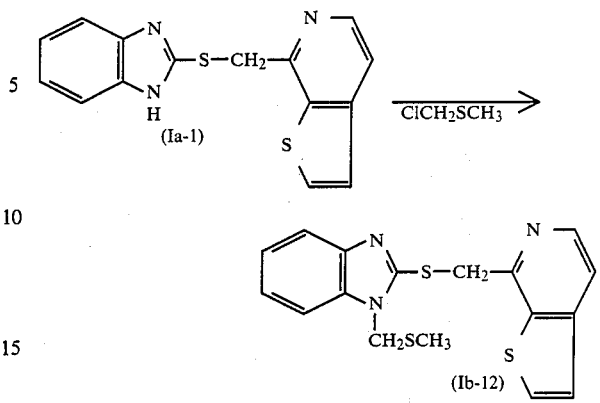

To a solution of 0.744 g Compound (Ia-1) is 8 ml of DMF was added 0.11 g of 60% NaH (oily substnace) under ice-cooling, and the mixture was stirred for 20 min. To the mixture was added 0.257 g of chloromethyl methyl sulfide. After gradually bringing back to room temperature, the mixture was stirred for 3 hr. DMF was evaporated under reduced pressure, and the residue was extracted with CHCl$_3$ and washed with water. The CHCl$_3$ layer was dried, and CHCl$_3$ was distilled off. The residue was subjected to silica gel column chromatography, eluting with a solution of CHCl$_3$ : AcOEt = 1 : 1 v/v. The eluted fraction gave 0.48 g (Yield : 53.7%) of 1-(methylthiomethyl)-2-[(thieno[2, 3-c]pyridin-7-yl)methylthio]benzimidazole (Ib-12) as an objective compound.

Melting point : 133 - 135° C. (recrystallized from AcOEt)

Anal. Calcd. (%) for C$_{17}$H$_{15}$N$_3$S$_3$ :

C, 57.11; H, 4.23; N, 11.75; S, 26.90.

Found (%) : C, 56.95; H, 4.22; N, 11.53; S, 26.98.

EXAMPLE 47

Synthesis of 1-(methylsulfinylmethyl)-2-[(thieno[2, 3-c]pyridin-7-yl]methylthio]benzimidazole (Ib-13)

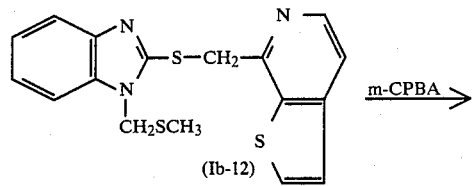

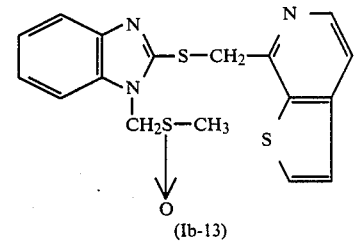

To a solution of 0.45 g of Compound (Ib-12) in 20 ml of CHCl$_3$ was added 0.27 g of 80% m-CPBA at -10° C., and the mixture was stirred for 30 min., and then neutralized with saturated aqueous NaHCO$_3$. After drying the CHCl$_3$ layer, CHCl$_3$ was distilled off. The residue was subjected to silica gel column chromatography, eluting with a solution of CHCl₃ : MeOH = 10 : 1 v/v. The eluted fraction gave 0.45 g (Yield : 95.7%) of 1-(methylsulfinylmethyl)2-[(thieno[2,3-c]pyridin-7-yl)methylthio]benzimidazole (Ib-13) as an objective product.

Melting point : 200 - 204° C. (d) (recrystallized from EtOH)

Anal. Calcd. (%) for $C_{17}H_{16}N_3S_3O$ :
C, 54.64; H, 4.05; N, 11.25; S, 25.75
Found (%) : C, 54.54; H, 3.94; N, 11.03; S, 25.51

EXAMPLE 48

Synthesis of 1-(chloroacetoxymethyl)-2-[(thieno[2,3-c]pyridin-7-yl)methylthio]benzimidazole (Ib-14)

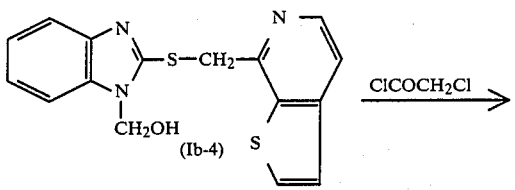

To a solution of 1.18 g of Compound (Ib-4) in 10 ml of pyridine was added 0.54 ml of chloroacetyl chloride under ice-cooling. After gradually bringing back to room temperature, the mixture was stirred for 1.5 hr. After evaporating pyridine under reduced pressure, the residue was extracted with CHCl₃ and washed with water. The CHCl₃ layer was dried, and CHCl₃ was distilled off. The residue was subjected to silica gel column chromatography, eluting with AcOEt. The eluted fraction gave 0.37 g (Yield : 23.0%) of an objective product, 1-(chloroacetoxymethyl)-2-[(thieno[2,3-c]pyridin-7-yl)methylthio]benzimidazole (Ib-14) as powder.

NMR: $\delta^{CDCl_3}$ 4.02 (s, 2H); 5.09 (s, 2H); 6.16 (s, 2H); 7.17–7.80 (m, 7H); 8.47 (d, 1H)

EXAMPLE 49

Synthesis of 1-(2-hydroxy-1-propenyl)-2-[(thieno[2,3-c]pyridin-7-yl]methylsulfinyl]benzimidazole (Ic-28)

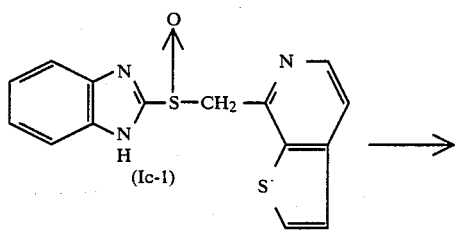

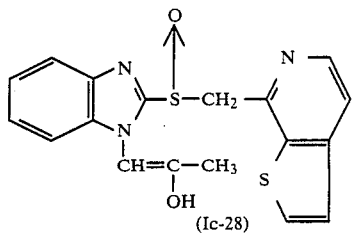

To a solution of 0.627 g of Compound (Ic-1) in 7 ml of DMF was added 0.088 g of 60% NaH (oily substance), and the mixture was stirred for 20 min. After ice-cooling, 0.194 g of monochloroacetone was added thereto; and after gradually bringing back to room temperature, the mixture was stirred for 4 hr. and allowed to stand overnight. DMF was evaporated under reduced pressure, and the residue was extracted with CHCl₃ and washed with water. The CHCl₃ layer was dried, and CHCl₃ was distilled off. The residue was subjected to silica gel column chromatography, eluting with AcOEt. The eluted fraction gave 0.31 g (Yield : 41.9%) of 1-(2-hydroxy-1-propenyl)-2-[(thieno[2,3-c]pyridin-7-yl)methylsulfinyl]benzimidazole (Ic-28) as an objective product.

Melting point : 187 - 192° C. (d) (recrystallized from EtOH)

Anal. Calcd. (%) for $C_{18}H_{15}N_3S_2O_2$ :
C, 58.52; H, 4.09; N, 11.37; S, 17.36.
Found (%) : C, 58.41; H, 4.30; N, 11.70; S, 17.12.

EXAMPLES 50–51

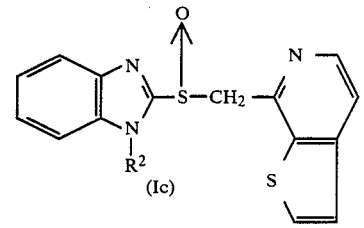

(wherein R² has the same meaning as defined above. X is halogen.)

The reactions were performed under the conditions shown in Table 11 as in Example 49, whereby the objective compounds (Ic) were obtained.

TABLE 11

| Ex. No. | Amount of Ic-1 (mg) | Amount of DMF (ml) | Amount of 60% NaH (mg) | R² | X | Reaction Time at Room Temp. (hr) | Compound No. of (Ic) |
|---|---|---|---|---|---|---|---|
| 50 | 380.0 | 4 | 53 | —CH₂NHCOPh | Cl | 1.5 | Ic-29 |

TABLE 11-continued

| 51 | 313.0 | 4 | 44 | 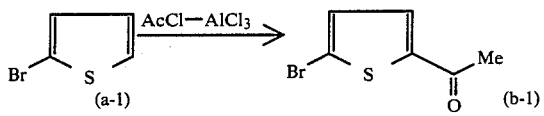 | Br | 3 | Ic-30 |

| Ex. No. | Yield of Ic (mg) (Yield: %) | M.P. (°C.) | Molecular Formula | Elementary Analysis (%) Up: Calcd. Down: Found | | | |
|---|---|---|---|---|---|---|---|
| | | | | C | H | N | S |
| 50 | 310.0 (57.4) | 158–160 (d) | $C_{23}H_{18}N_4S_2O_2$ | 61.86 61.74 | 4.06 4.20 | 12.55 12.37 | 14.35 14.36 |
| 51 | 380.0 (80.4) | 175–177 (d) | $C_{24}H_{26}N_4S_2O_3$ | 61.00 61.06 | 3.41 3.35 | 11.86 11.67 | 13.57 13.56 |

REFERENTIAL EXAMPLE 1
2-Acetyl-5-bromothiophene (b-1)

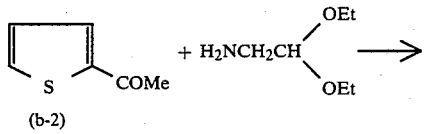

When 1.56 ml (1.1 equivalents) of acetyl chloride was added to a solution of 3.26 g (0.02 mmol) of 2-bromothiophene in 30 ml of $CH_2Cl_2$, the mixture foamed and turned black. After stirring for 1 hr. at room temperature, the mixture was mixed with ice and concentrated hydrochloric acid. While being decolored with active carbon, the mixture was extracted with $CH_2Cl_2$, whereby 3.53 g (Yield : 86.1%) of the objective product, 2-acetyl-5-bromothiophene (b-1) was obtained as colorless crystals.

MNR : $\delta^{CDCl_3}$ 2.50 (s, 3H); 7.10 (m, 1H); 7.43 (m, 1H)

REFERENTIAL EXAMPLE 2
[(α-Methyl-2-thenylidene)amino]acetaldehyde diethyl acetal (c-1)

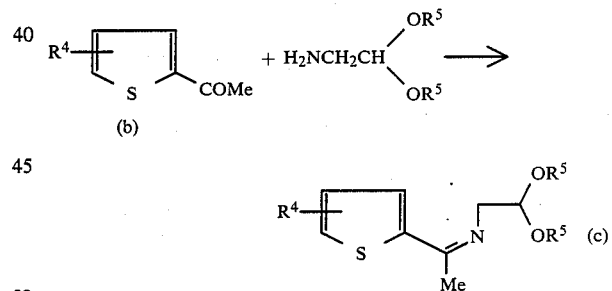

To 21.70 g (0.172 mol) of 2-acetylthiophene (b-2) were added 38 ml of toluene and 25.22 g (0.189 mol) of aminoacetaldehyde diethylacetal, and the mixture was refluxed for 24 hr., using a dehydrating tube filled with Molecular Sieves 4A. The residue was distilled to give 31.43 g (Yield : 75.7%) of the objective product, [(δ-methyl-2-thenylidene)amino]acetaldehyde diethyl acetal (c-1) as yellow liquid.

Boiling point : 107.0° C./0.06 mmHg - 121.0° C./0.075 mmHg

REFERENTIAL EXAMPLES 3–6

(wherein $R^4$ has the same meaning as defined above. $R^5$ is methyl or ethyl.)

The reactions were performed under the conditions shown in Table 12 as in Referential Example 1, whereby the objective compounds (c) were obtained.

TABLE 12

| Ref. No. | $R^4$ | Compd. No. | Amount of b (g) | Amount of $H_2NCH_2CH(OR^5)(OR^5)$ (ml) | $R^5$ | Amount of Toluene (ml) | Reaction Time (hr) | Compd. No. | Yield (g) (Yield: %) | Properties | Appearance |
|---|---|---|---|---|---|---|---|---|---|---|---|
| 3 | 5-Me | b-3 | 8.7 | 8.11 | Me | 30 | 70 | c-2 | 8.19 (58.1) | Boiling point: 136–140° C./0.7 mmHg | Liquid |
| 4 | 5-Et | b-4 | 9.8 | 8.30 | Me | 60 | 65 | c-3 | 7.24 (47.2) | Boiling point: 138–140° C./0.7 mmHg | Liquid |
| 5 | 4-Me | b-5 | 9.9 | 9.23 | Me | 30 | 25 | c-4 | 9.10 (56.7) | Boiling point: 113–118° C./0.2 mmHg | Liquid |

TABLE 12-continued

| Ref. No. | R[4] | Compd. No. | Amount of b (g) | H$_2$NCH$_2$CH(OR$^5$)(OR$^5$) R$^5$ (ml) | Amount of Toluene (ml) | Reaction Time (hr) | Compd. No. | Yield (g) (Yield: %) | Properties | Appearance |
|---|---|---|---|---|---|---|---|---|---|---|
| 6 | 5-Br | b-1 | 3.53 | 2.75  Et | 10 | 20 | c-5 | 6.12 (Mixture with b-1) | NMR: $\delta^{CDCl_3}$ 2.13 (s, 3H) | Oily substance |

REFERENTIAL EXAMPLE 7

2-Acetylaminoethylthiophene (f-1)

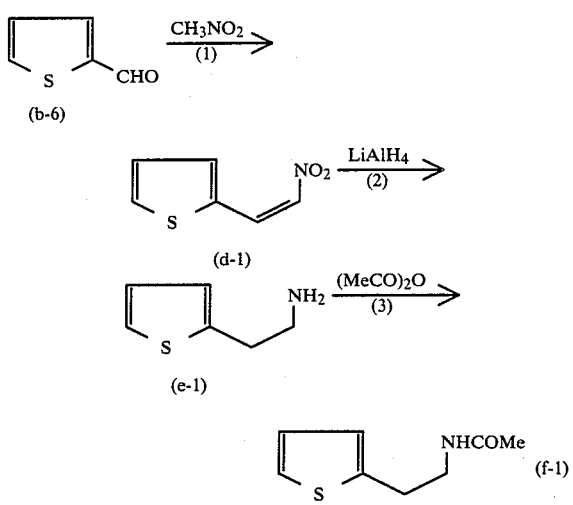

(1) To 7.85 g (0.07 mol) of 2-thiophenecarboxaldehyde were added 148 ml of MeOH and 12.82 g (0.210 mol) of CH$_3$NO$_2$; and 74 ml of 50% aqueous solution of NaOH was added dropwise to the mixture with stirring at -5° C. After being stirred at 10° C. for 1 hr., the reaction solution was poured into a mixture of 296 ml of 36% HCl and 493 ml of water at 0° C. The crystals separating out were collected by filtration and washed with water, whereby 6.65 g (Yield : 61.2%) of the objective compound, 2-(2-nitroethenyl)thiophene (d-1) was obtained as greenish brown crystals.

IR : (CHCl$_3$) 1330, 1620, 1500 cm-1
NMR : $\delta^{CDCl_3}$ 7.07 - 7.57 (m, 3H); 7.46 (d, 1H); 8.14 (d, 1H)

(2) To a solution of 6.64 g (0.175 mol) of LiAlH$_4$ in ether was added dropwise a mixture of 6.32 g (0.0407 mol) of Compound (d-1) obtained in (1) and 90 ml of dry ether at room temperature. After being refluxed for 5 hr., the mixture was mixed with 4.4 ml of AcOEt, 50 ml of hydrous ether and 25 ml of water in order under ice-cooling. After stirring the mixture for 1 hr. at room temperature, the insoluble material was filtered off with a filter aid, and the residue was washed with ether. The filtrate was combined with washings and dried over anhydrous sodium sulfate. The solvent was evaporated under reduced pressure, whereby 4.92 g (Yield : 95.0%) of the objective compound, 2-(2-aminoethyl)thiophene (e-1) was obtained as dark red liquid.

IR : (CHCl$_3$) 2930, 1590, 1430 cm-1
NMR: $\delta^{CDCl_3}$ 1.61 (s, 2H); 2.97 (s, 4H); 6.78 - 7.17 (m, 3H)

(3) To 4.90 g (0.0385 mol) of Compound (e-1) obtained in (2) was added 73 ml (0.445 mol) of aqueous 20% NaOH, and 18.48 g (0.181 mol) of acetic anhydride was dropwise added to the mixture with stirring at room temperature. After being stirred for 1 hr., the mixture was extracted with benzene. The benzene layer was washed with saturated brine and dried over anhydrous sodium sulfate. The solvent was evaporated under reduced pressure to give 6.60 g of liquid. The liquid was subjected to silica gel column chromatography, eluting with AcOEt, and the eluate gave 5.71 g (Yield : 87.6%) of the objective product, 2-acetylaminoethylthiophene (f-1) as brown crystals.

IR : (CHCl$_3$) 1665, 1510, 3450 cm$^{-1}$
NMR: ° C.DCl$_3$ 1.96 (s, 3H); 3.02 (t, 2H); 3.52 (q, 2H); 5.73 (b, 1H); 6.77–7.20 (m, 3H)

REFERENTIAL EXAMPLE 8

4-Methyl-6, 7-dihydrothieno[3, 2-c]pyridine (g-1)

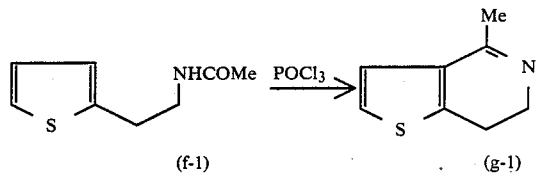

To 5.70 g (0.0337 mol) of 2-acetylaminoethylthiophene (f-1) was added 157 ml of dry benzene; and while being refluxed, a mixture of 13.80 g (0.09 mol) of phosphorus oxychloride and 63 ml of dry benzene was added dropwise to the solution. After being refluxed for 2 hr., the mixture was cooled with ice, and the reaction solution was poured into 315 g of ice. Under ice-cooling, the mixture was adjusted to pH 10 or more with 48% aqueous NaOH, and the solution was extracted with ether. After being washed with saturated brine, the ether layer was dried over anhydrous sodium sulfate. The solvent was concentrated under reduced pressure to give 4.45 g (Yield : 87.3%) of the objective product, 4-methyl-6, 7-dihydrothieno[3, 2-c]pyridine (g-1) as dark red liquid.

IR : (CHCl$_3$) 1625, 1280, 1380 cm$^{-1}$
NMR: $\delta^{CDCl_3}$ 2.30 (s, 3H); 2.80 (t, 2H); 3.73 (t, 2H); 7.08 (s, 2H)

REFERENTIAL EXAMPLE 9

7-Methylthieno[2, 3-c]pyridine (h-1)

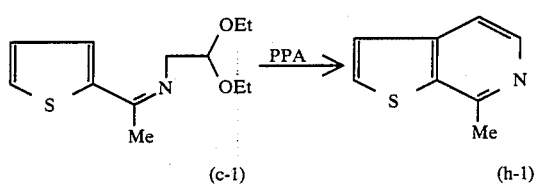

250 g of polyphosphoric acid was heated at 120° C. under stirring and dropwise mixed with 12.07 g (0.05 mol) of [(δ-methyl-2-thenylidene)amino]acetaldehyde diethyl acetal (c-1). After being stirred for 20 min. at 120° C., the solution was cooled to room temperature and poured into 300 g of ice. The solution was shaken with ether to remove by-products. Under ice-cooling, the aqueous layer was adjusted to pH 10 or more with 30% aqueous NaOH and extracted with ether. The ether layer was washed with saturated brine and dried over anhydrous sodium sulfate. Concentration under reduced pressure gave 6.38 g of brown liquid. The liquid was subjected to silica gel column chromatography, whereby 5.86 g (Yield : 78.5%) of the objective produce, 7-methylthieno[2, 3-c]pyridine (h-1) was obtained as brown liquid.

IR : (CHCl₃) 1580, 830, 1380 cm⁻¹
NMR: $\delta^{CDCl_3}$ 2.80 (s, 3H); 7.35 (d, 1H); 7.53 (d, 1H); 7.64 (d, 1H); 8.41 (d, 1H)

REFERENTIAL EXAMPLE 10

2-Bromo-7-methylthieno[2, 3-c]pyridine (h-2)

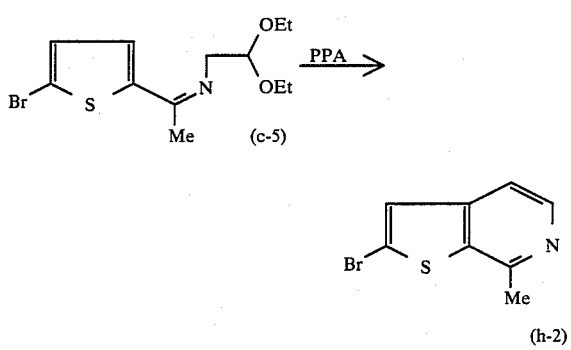

15 ml of polyphosphoric acid was heated at 120° C. under stirring and dropwise mixed with 3.00 g of a mixture containing c-5 obtained in Referential Example 6 in 5 min. The mixture was stirred for 30 min., mixed with 100 ml of ice water, and washed with ether. The aqueous layer was adjusted to pH 8 with aqueous NaOH and extracted with ether, whereby 397 mg of the objective compound, 2-bromo-7-methylthieno[2, 3-c]-pyridine (h-2) was obtained. (Yield from the above mixture : 20.6%)

NMR: $\delta^{CDCl_3}$ 2.75 (s, 3H); 7.37 (s, 1H); 7.43, 8.40 (ABq, J=6Hz, 2H).

REFERENTIAL EXAMPLE 11

7-Methylthieno[2, 3-c]pyridine (h-1)

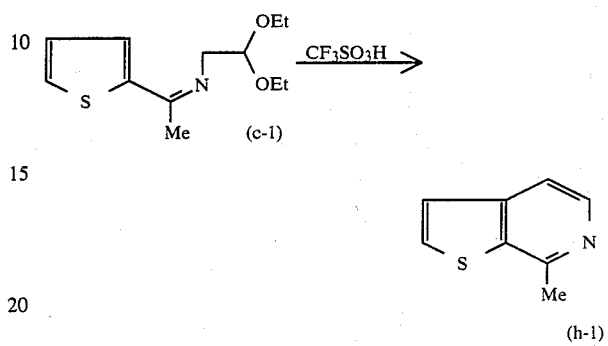

To 7.07 ml (4 equivalents) of trifluoromethanesulfonic acid heated at 128° C. was added dropwise 4.82 g (0.02 mol) of Compound (c-1) for 4 min. At this time, the internal temperature rose to 155° C. After completion of the addition, the solution was stirred for 5 min. (bath temperature 135° C.). After bringing its temperature down to room temperature, the solution was mixed with ice water and extracted with ether. The aqueous layer was adjusted to pH 8 with aqueous NaHCO₃ and extracted with ether, whereby 2.227 g of an oily substance was obtained. This was subjected to silica gel column chromatography (silica gel : 50 g), eluting with CH₂Cl₂ —Ethyl acetate (10:1–1:1 v/v), whereby 1.906 g (Yield : 63.9%) of the objective product, 7-methylthieno[2, 3-c]pyridine (h-1) was obtained.

REFERENTIAL EXAMPLE 12–14

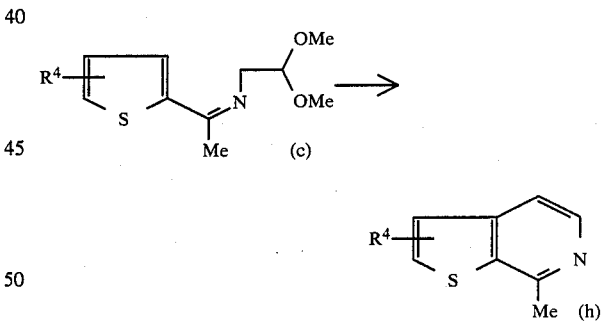

(where in R⁴ has the same meaning as defined above).

The reactions were performed under the conditions shown in Table 13 as in Referential Example 11, whereby the objective compounds (h) were obtained. But CF₃SO₃H was heated at 128° C. in advance, and CHCl₃—AcOEt (1 : 1 v/v) was used as an eluent.

TABLE 13

| Ex. No. | R⁴ | Amount of c Compd. No. | (g) | Amount of CF₃SO₃H (g) | Reaction Time (min) | Reaction Temp. (°C.) | Compd. No. | Yield (g) (Yield: %) | Properties |
|---|---|---|---|---|---|---|---|---|---|
| 12 | 5-Me | c-2 | 8.14 | 25 | 5 | 125 | h-3 | 3 (51.3) | Appearance: highly viscous |
| 13 | 5-Et | c-3 | 7.18 | 25 | 5 | 125 | h-4 | 1.15 (21.8) | Appearance: highly viscous |
| 14 | 4-Me | c-4 | 8.90 | 25 | 5 | 120 | h-5 | 4.30 | Melting point: 55–57° C. |

TABLE 13-continued

| Ex. No. | R⁴ | Amount of c Compd. No. | (g) | Amount of CF₃SO₃H (g) | Reaction Time (min) | Reaction Temp. (°C.) | Compd. No. | Yield (g) (Yield: %) | Properties |
|---|---|---|---|---|---|---|---|---|---|
| | | | | | | | | (67.3) | (recrystallized from n-hexane) Anal. Calcd. (%) for $C_9H_9NS$: C, 66.22; H, 5.56 N, 8.58; S, 19.64 Found (%): C, 66.46; H, 5.71 N, 8.62; S, 19.81 |

REFERENTIAL EXAMPLE 15

3-Bromo-7-bromomethylthieno[2, 3-c]pyridine (i-1)

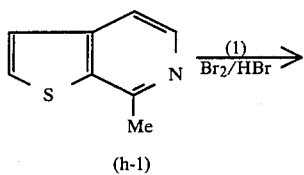

(h-1)

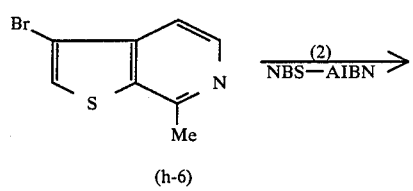

(h-6)

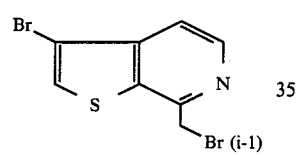

Br (i-1)

(1) To a solution of 5.68 g (0.0381 mol) of Compound (h-1) in 210 ml of 48 % HBr at room temperature was added dropwise a mixture of 2.55 ml (1.1 equivalents) of bromine and 105 ml of 48% HBr. Further the solution was heated for 10 hr. at 100 ° C. (bath temp.). After bringing the temperature down to room temperature, it was mixed with ice water. The solution was made alkaline with 28% aqueous NH₄OH and extracted with CH₂Cl₂, whereby 8.17 g of crude crystals were obtained. The crude cyrstals were recrystallized from a mixture of CH₂Cl₂—methanol, whereby 6.19 g (Yield : 71.2 %) of Compound (h-6) was obtained.

NMR: $\delta^{CDCl_3}$2.80 (s, 3H); 7.56, 8.54 (ABq, 2H, J=6Hz); 7.65 (s, 1H)

(2) A mixture of 228 mg (1 mmol) of Compound (h-6) obtained in (1), 187 mg (1.05 equivalents) of NBS, 5 mg of AIBN, and 8 ml of carbon tetrachloride was refluxed for 1.5 hr. The mixture was further mixed with 187 mg (1.05 equivalents) of NBS, 5 mg of AIBN, and 8 ml of carbon tetrachloride and refluxed for 1.5 hr. The precipitating insoluble material was removed by filtration, and the filtrate was subjected to silica gel column chromatography silica gel : 40 g), eluting with CH₂Cl₂, whereby 174 mg (Yield : 56.7 %) of the objective produce, 3-bromo-7-bromoethylthieno[2, 3-c]pyridine (i-1) was obtained.

NMR: $\delta^{CDCl_3}$4.82 (s, 2H); 7.72 (m, 2H); 8.05 (m, 1H)

REFERENTIAL EXAMPLE 16

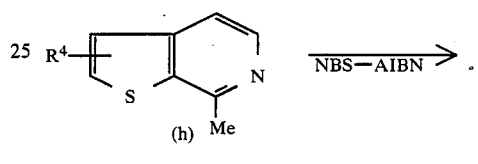

(h) Me

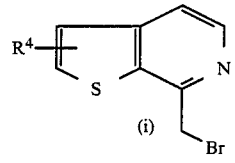

(i) Br (wherein R⁴ has the same meaning as defined above).

The reactions were performed under the conditions shown in Table 14 as in Referential Example 15-(2), whereby the objective compound (i) was obtained.

TABLE 14

| Ex. No. | Compd. No. | Amount of h R⁴ | (mg) (mmol) | Amount of NBS (mg) (mmol) | Amount of AIBN (mg) | Amount of CCl₄ (ml) | Reaction Time (hr) | Compd. No. | Yield (mg) (Yield: %) | Properties |
|---|---|---|---|---|---|---|---|---|---|---|
| 16 | h-2 | 2-Br | 456 (2) | 712 (4) | 5 | 32 | 7.5 | i-2 | 100 (16.3) | NMR: δCDCl₃4.74 (s, 3H); 7.40 (s, 1H); 7.51, 8.45 (ABq, J = 6Hz, 2H) |

REFERENTIAL EXAMPLE 17

4-Methylthieno[3, 2-c]pyridine (j-1)

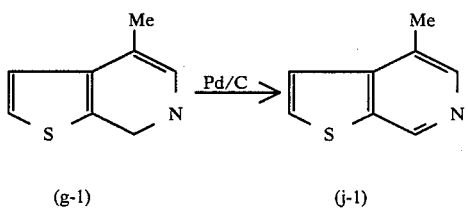

(g-1)   (j-1)

To 4.43 g (0.0293 mol) of 4-methyl-6, 7-dihydrothieno[3, 2-c]pyridine (g-1) were added 244 ml of dry xylene and 3.42 g of 10% palladium carbon, and the mixture was refluxed for 34 hr. After being cooled down to room temperature, the solution was filtered. The filtrate was concentrated under reduced pressure and subjected to silica gel column chromatography, eluting with AcOEt - MeOH, whereby 1.47 g (Yield : 33.6%) of the objective product, 4-methylthieno[3, 2-c]pyridine (j-1) was obtained as brown liquid.

IR (CHCl$_3$): 1430, 1575, 900 cm$^{-1}$

NMR : $\delta^{CDCl_3}$ 2.86 (s, 3H); 7.49 (s, 2H); 7.66 (d, 1H); 8.34 (d, 1H)

REFERENTIAL EXAMPLE 18

7-Chloromethyl-3-cyanothieno[2, 3-c]pyridine (i-4)

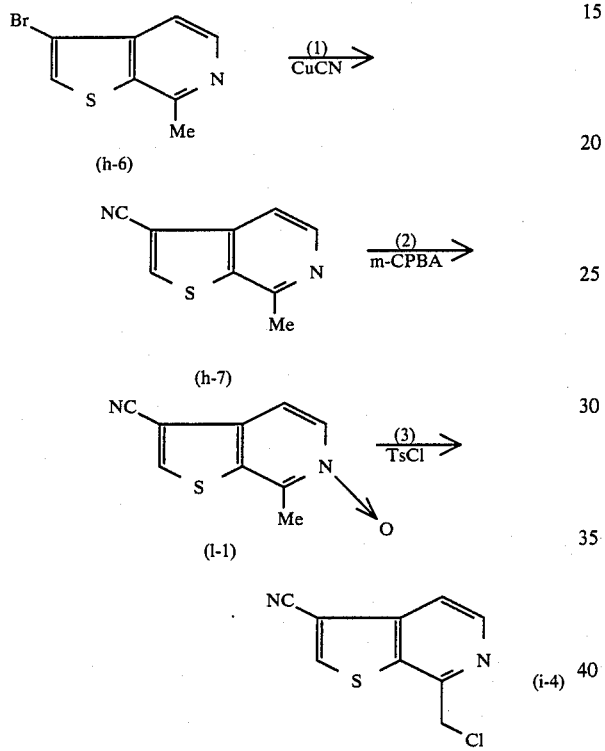

(1) A mixture of 4.56 g (0.02 mol) of Compound (h-6), 6.09 g (3 equivalents) of CuCN, 35 ml of anhydrous DMF and 35 ml of benzonitrile was refluxed for 25 hr. at 180° C. (bath temperature) with stirring. To the solution was added 28% aqueous ammonia, and the insoluble material was removed by filtration. The filtrate was extracted with CH$_2$Cl$_2$, subjected to silica gel column chromatography (silica gel : 120 g), eluting with dichloromethane—ethyl acetate, and washed with ether, whereby 2.39 g (Yield : 68.6%) of the objective product, 3-cyano-7-methylthieno[2, 3-c]pyridine (h7) was obtained.

NMR: $\delta^{CDCl_3}$ 2.83 (s, 3H); 7.72, 8.60 (ABq, J=6Hz, 2H);
8.29 (s, 1H)

(2) To a solution of 870 mg (5 mmol) of Compound (h-7) in 40 ml of dichloromethane was added 1.188 g (1.1 equivalents) of 80% m-CPBA in 3 min. under ice-cooling. After stirring for 2 hr. at room temperature, 108 mg (0.1 equivalent) of the peracid was further added to the mixture, which was allowed to react for 1 hr. The solution was mixed with 10% aqueous Na$_2$SO$_3$ and saturated aqueous NaNCO$_3$ and extracted with dichloromethane, whereby 942 mg (Yield : 99.0%) of the objective product, 3-cyano-7-methylthieno[2, 3-c]pyridine N-oxide (l-1) was obtained.

IR : $\nu_{max}^{Nujol}$ 2220, 1265 cm$^{-1}$

NMR: $\delta^{CDCl_3}$ 2.80 (s, 3H); 7.70, 8.40 (ABq, J=7Hz, 2H);
8.25 (s, 1H)

(3) To a mixture of 378 mg (1.99 mmol) of Compound (l-1) in 30 ml of anhydrous benzene was added dropwise a mixture of 568 mg (1.5 equivalents) of TsCl and 7 ml of anhydrous benzene in 5 min. under refluxing, and then the mixture was refluxed for 4 hr. The reaction solution, after concentration under reduced pressure, was subjected to silica gel column chromatography (silica gel : 60 g), eluting witih CH$_2$Cl$_2$ - methanol, whereby 287 mg (Yield : 69.2%) of the objective product, 7-chloromethyl-3-cyanothieno[2, 3-c]pyridine (i-4) was obtained.

NMR : $\delta^{CDCl_3}$ 5.00 (s, 2H); 7.90, 8.67 (ABq, J=6Hz, 2H): 8.40 (s, 1H)

REFERENTIAL EXAMPLE 19

3-Carboxy-7-chloromethylthieno[2, 3-c]pyridine (i-5)

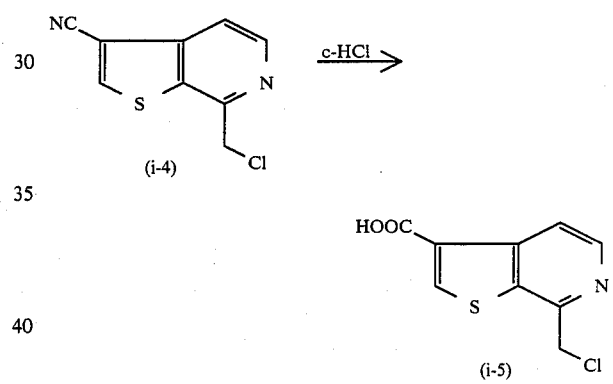

A solution of 243 mg (1.16 mmol) of Compound (i-4) in c-HCl was refluxed for 4 hr. When the solution was adjusted to pH 4 with aqueous NaHCO$_3$, crystals precipitated. The crystals were collected by filtration and dried, whereby 220 mg (Yield : 83.3%) of the objective product, 3-carboxy-7-chloromethythieno[2, 3-c]pyridine (i-5) was obtained.

IR : $\nu_{max}^{Nujol}$ 1700 cm$^{-1}$

NMR: $\delta_{d6\text{-}DMSO}^{CDCl_3}$ 5.03 (s, 2H); 8.42, 8.56 (ABq, J=5Hz, 2H); 8.84 (s, 1H)

REFERENTIAL EXAMPLE 20

3-Carbamoyl-7-chloromethylthieno[2, 3-c]pyridine (i-6)

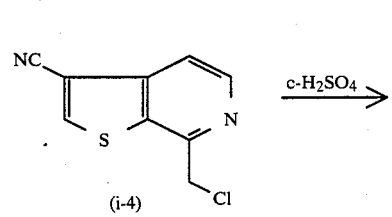

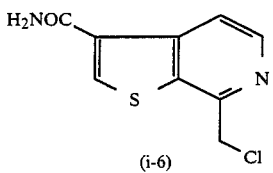

A solution of 287 mg (1.38 mmol) of Compound (i-4) in 8 ml of conc. sulfuric acid was stirred for 50 min. at 40 °C. (bath temperature). When the solution was adjusted to pH 8 with aqueous NaHCO$_3$, crystals precipitated. The crystals were collected by filtration and dried, whereby 220 mg (Yield : 70.6%) of the objective product, 3-carbamoyl-7-chloromethylthieno[2, 3-c]pyridine (i-6) was obtained as crystals.

IR : $\nu_{max}^{Nujol}$ 3300, 3075, 1660 cm$^{-1}$

NMR : $\delta_{d6\text{-}DMSO}^{CDCl_3}$ 5.00 (s, 2H); 8.50 (s, 2H); 8.75 (s, 1H)

REFERENTIAL EXAMPLE 21

7-Chloromethyl-2-methylthieno[2, 3-c]pyridine (i-7)

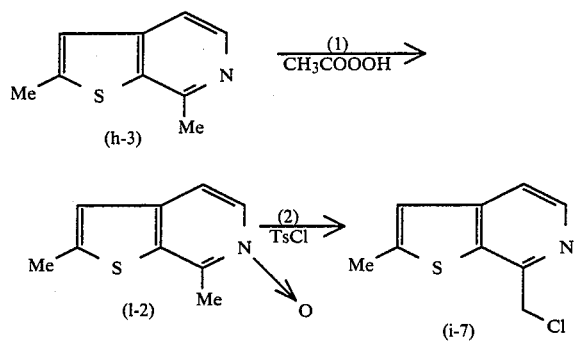

(1) To a solution of 2.9 g of Compound (h-3) in 50 ml of CHCl$_3$ was added 3.9 g of 40% peracetic acid at -10° C. After gradually bringing down to room temperature, the solution was stirred for 3 hr. and neutralized with aqueous NaHCO$_3$. The CHCl$_3$ layer was dried, and CHCl$_3$ was evaporated. Ethyl ether was added to the residue, and the precipitated compound was collected by filtration, whereby 3.01 g (Yield : 95.7%) of the objective produce, 2-methyl-7-methylthieno[2, 3-c]pyridine N-oxide (1-2), was obtained as crystals.

Melting point : 125–127° C. (recrystallized from AcOEt)

Anal. Calcd. (%) for C$_9$H$_9$NSO·0.7 H$_2$O :
C, 56.35; H, 5.46; N, 7.30; S, 16.71.
Found (%) : C, 56.37; H, 5.52; N, 7.37; S, 16.70.

(2) To a solution of 2.5 g of Compound (1-2) obtained in (1) in 70 ml of benzene was added dropwise a mixture of 3.19 g of TsCl in 40 ml of benzene under refluxed with heating, and the mixture was refluxed with heating for 1 hr. After cooling, the solution was neutralized with saturated aqueous NaHCO$_3$. The benzene layer was dried and concentrated. The resudue was subjected to silica gel column chromatography, eluting with AcOEt. The eluted fraction gave 1.86 g (Yield : 67.0%) of the objective product, 7-chloromethyl-2-methyl-thieno[2, 3-c]pyridine (i-7) was obtained.

NMR: $\delta^{CDCl_3}$ 2.64 (s, 3H); 4.87 (s, 2H); 7.03 (bs, 1H); 7.46 (d, J=6Hz, 1H); 8.39 (d, J=6Hz, 1H)

REFERENTIAL EXAMPLES 22–23

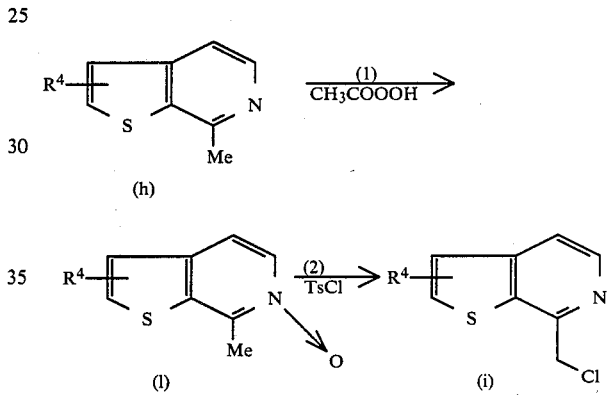

(wherein R$^4$ has the same meaning as defined above).

The reactions were performed under the conditions shown in Tables 15 and 16 as in Referential Example 21, whereby the objective compounds (i) were obtained.

TABLE 15

| | | | | | (Reaction (1)) | | | |
|---|---|---|---|---|---|---|---|---|
| Ex. No. | Amount of h | | | Amount of CHCl$_3$ (ml) | Amount of CH$_3$COOOH (g) | No. of objective compd. | Yield (g) (Yield: %) | M.P. (°C.) | Properties |
| | R$^4$ | (g) | Compd. No. | | | | | | |
| 23 | 2-Et | 1.1 | h-4 | 20 | 1.36 | 1-3 | 1.08 (90.0) | — | NMR: $\delta$CDCl$_3$ 1.38 (t, J = 7Hz, 3H); 2.73 (s, 3H); 2.96 (q, J = 7Hz, 2H); 6.98 (bs, 1H); 7.35 (db, J = 6Hz, 1H); 8.20 (d, J = 6Hz, 1H) |
| 24 | 3-Me | 4.08 | h-5 | 75 | 5.30 | 1-4 | 3.86 (86.2) | 166–168 | Anal. Calcd. (%) for C$_9$H$_9$NSO: C, 60.31; H, 5.06; N, 7.81; S, 17.89 Found (%): C, 60.23; H, 5.17; N, 7.77; S, 18.04 |

TABLE 16

| | | | | | (Reaction (2)) | | | |
|---|---|---|---|---|---|---|---|---|
| Ex. No. | Amount of 1 | | Compd. No. | Amount of Benzene (ml) | Amount of TsCl (g) | Amount of Benzene for dropping (ml) | No. of objective compd. | Yield (g) (Yield: %) | Properties |
| | $R^4$ | (g) | | | | | | | |
| 23 | 2-Et | 1.02 | 1-3 | 30 | 1.2 | 15 | i-8 | 0.77 (68.8) | NMR: δCDCl$_3$ 1.41 (t, J = 7Hz, 3H); 2.98 (q, J = 7Hz, 2H); 4.87 (s, 2H); 7.06 (s, 1H); 7.48 (d, J = 6Hz, 1H); 8.41 (d, J = 6Hz, 1H) |
| 24 | 3-Me | 3.58 | 1-4 | 100 | 4.56 | 60 | i-9 | 2.53 (64.1) | NMR: δCDCl$_3$ 2.45 (s, 3H); 4.93 (s, 2H); 7.3–7.4 (m, 1H); 7.57 (d, J = 6Hz, 1H); 8.52 (d, J = 6Hz, 1H) |

REFERENTIAL EXAMPLE 24

3-Acetylamino-7-methylthieno[2,3-c]pyridine N-oxide (1-5)

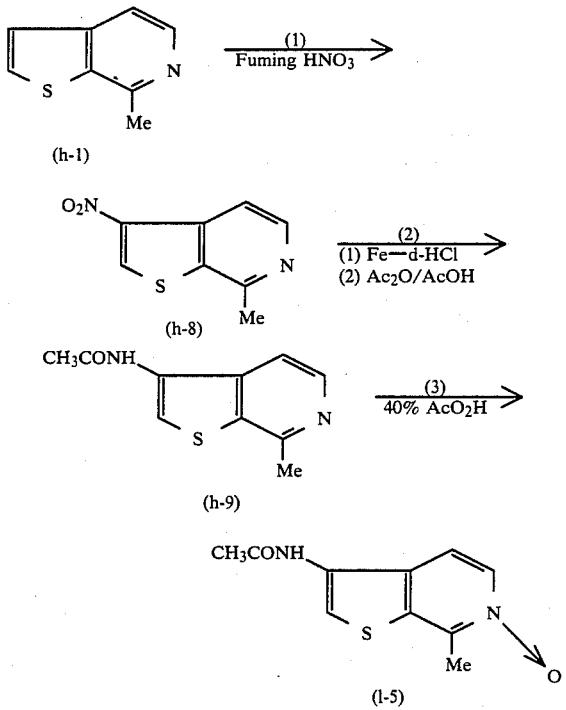

(1) To 1.49 g (0.01 mol) of Compound (h-1) was added dropwise 5.3 ml of conc. sulfuric acid in 10 min. under ice-cooling to give a solution. To the solution was added dropwise a mixture of 5.3 ml (11.9 equivalents) of 94 % fuming nitric acid and 5.3 ml of conc. sulfuric acid in 15 min. below 30° C., and then the mixture was stirred for 2 hr. at 90 ° C. The reaction mixture was poured into ice water, and the solution was adjusted to pH 11 with 10% NaOH and extracted with CH$_2$Cl$_2$. The organic layer gave 0.97 g of crude crystals. The crystals were subjected to silica gel column chromatography (silica gel : 60 g), eluting with a solution of CH$_2$Cl$_2$ - AcOEt (10 : 1–1 : 1 v/v), whereby 0.88 g (Yield : 45.3%) of the objective product, 3 nitro-7-methylthieno[2,3-c]pyridine (h-8) was obtained as crystals. When this reaction was performed at 0° C. in 1 hr., the yield increased to 90.9%.

NMR: δ$^{CDCl_3}$ 2.83 (s, 3H); 8.29, 8.64 (ABq, J=6Hz, 2H); 8.85 (s, 1H)

(2) A mixture of 0.44 g (2.27 mmol) of Compound (h-8) obtained in (1), 0.38 g (3 equivlents) of iron powder, 8 ml of MeOH, 4 ml of water and 0.5 ml of 10% HCl was stirred for 1 hr. under refluxing. The inorganic material was removed by filtration using a filter aid. The filtrate was concentrated to dryness, whereby 446 mg was obtained as a residue. To the residue were added 5 ml of acetic acid and 0.86 ml (4 equivalents) of acetic anhydride, and the mixture was refluxed for 1 hr. The solution was concentrated under reduced pressure and extracted with CH$_2$Cl$_2$. The extract was washed with saturated aqueous solution of NaHCO$_3$ and water, respectively. The organic layer gave 504 mg of crude crystals. The crystals were subjected to silica gel column chromatography (silica gel : 70 g), eluting with a solution of CH$_2$Cl$_2$ - MeOH (10 : 1 v/v), whereby 359 mg (Yield : 76.7%) of 3-acetylamino-7-methylthieno[2,3-c]pyridine (h-9) was obtained.

NMR: ° C.DCl$_3$ 2.23 (s, 3H); 2.75 (s, 3H); 7.42, 8.36 (ABq, J=6Hz, 2H); 8.16 (s, 1H)

(3) To a solution of 201 mg (0.974 mmol) of Compound (h-9) obtained in (2) in 15 ml of CH$_2$Cl$_2$ was added 290 mg (1.5 equivalents) of 40% peracetic acid at room temperature, and the mixture was stirred for 3 hr. as it was. After being neutralized with 10 % Na$_2$SO$_3$ and saturated aqueous NaHCO$_3$, the solution was concentrated to dryness, and the organic material was extracted with methanol. The isoluble material was removed by filtration, and the solution was concentrated again, whereby 648 mg of crude produce was obtained. The produce was subjected to silica gel column chromatography (silica gel : 35 g), eluting with a solution of CH$_2$Cl$_2$ MeOH (10 : 1 v/v), whereby 160 mg (Yield : 73.9%) of the objective produce, 3-acetylamino-7-methylthieno[2, 3-c]pyridine N-oxide (15) was obtained as crystals.

NMR : δ$_{d6-DMSO}^{CDCl_3}$ 2.19 (s, 3H); 2.61 (s, 3H); 8.03, 8.23 (ABq, J=8Hz, 2H); 8.12 (s, 1H)

REFERENTIAL EXAMPLE 25

7-Chloromethylthieno[2, 3-c]pyridine (i-10)

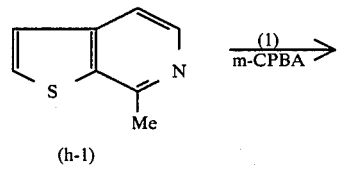

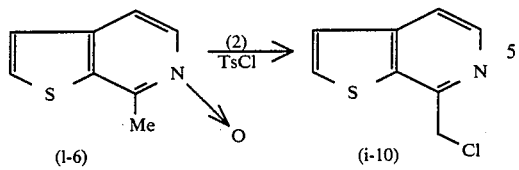

(1) To a solution of 298 mg (2 mmol) of Compound (h-1) in 5 ml of CH$_2$Cl$_2$ was added 474 mg (1.1 equivalents) of 80% m-CPBA at room temperature in 3 min., and the mixture was stirred for 2 hr. The solution was mixed with water and 5% NaOH and extracted with CH$_2$Cl$_2$. After washing with water, the organic layer was concentrated, whereby 271 mg (Yield : 82.1%) of 7-methylthieno[2, 3-c]pyridine N-oxide (l-6) was obtained as crystals.

NMR : $\delta^{CDCl_3}$2.80 (s, 3H); 7.32, 7.63 (ABq, J=5Hz, 2H); 7.52, 8.25 (ABq, J=7Hz, 2H)

Alternatively, a solution of 5.55 g of Compound (h-1) in 110 ml of CHCl, was mixed with 7.75 g of 40% peracetic acid under ice-cooling. After gradually bringing back to room temperature, the solution was stirred for 2 hr. and 15 min. The solution was neutralized with saturated aqueous NaHCO$_3$ and then saturated with brine. The CHCl$_3$ layer was separated and dried, and CHCl$_3$ was distilled off. The residue was subjected to silica gel column chromatography, eluting with a solution of CHCl$_3$ -MeOH (10 : 1 v/v). The eluted fraction gave 5.6 g (Yield : 91.0%) of the Compound (l-6) as an objective compound.

(2) To a solution of 265 mg (1.60 mmol) of Compound (l-6) obtained in (1) in 1.5 ml of CH$_2$Cl$_2$ were alternately added a solution of 369 mg (1.5 equivalents) of phosphorus oxychloride in 2.5 ml of CH$_2$Cl$_2$ and a solution of 236 mg (1.5 equivalents) of triethylamine in 2.5 ml of CH$_2$Cl$_2$ at a rate of 0.5 ml in about 4 min. at room temperature, and the solution was refluxed for 5 min. After being neutralized with saturated aqueous NaHCO$_3$, the solution was extracted with CH$_2$Cl$_2$. The extract was subjected to silica gel column chromato-graphy (silica gel : 30 g), eluting with CH$_2$Cl$_2$ ethyl acetate (10 : 1 v/v), whereby 154 mg (Yield : 52.4%) of 7-chloromethyl-thieno[2, 3-c]pyridine (i-10) was obtained as an oily substance.

NMR: $\delta^{CDCl_3}$4.97 (s, 2H); 7.42, 7.75 (ABq, J=6Hz, 2H); 7.67, 8.52 (ABq, J=6Hz, 2H)

Alternatively, 1.652 g (10.0 mmol) of Compound (l-6) was mixed with 50 ml of dry benzene to give a solution. Under refluxing, a mixture of 2.29 g (12.0 mmol) of TsCl and 30 ml of dry benzene was added dropwise to the solution. After being refluxed for 1 hr., the solution was cooled to room temperature and mixed with 20 ml of water and saturated aqueous NaHCO$_3$. The aqueous layer was salted out and extracted with CH$_2$Cl$_2$. The CH$_2$Cl$_2$ layer and the benzene layer were combined and allowed to stand overnight. The solvent layer, after being washed with saturated aqueous NaHCO$_3$, was dried over anhydrous sodium sulfate, and concentrated under reduced pressure, whereby 3.09 g of a crude product was obtained. The product was subjected to silica gel column chromatography, eluting with CH$_2$Cl$_2$ - AcOEt, whereby 1.421 g (Yield : 77.4%) of Compound (i-10) was obtained as light brown liquid.

| Formulation | |
|---|---|
| 2-[(thieno[2, 3-c]pyridin-7-yl)methylthio]-benzimidazole (Ia-1) | 25 mg |
| Lactose | 100 mg |
| Wheat starch | 15 mg |
| Gelatin | 5 mg |
| Magnesium stearate | 5 mg |
| Total | 150 mg |

The above ingredients were charged into a capsule to make a capsule.

EFFECT OF THE INVENTION

Antisecretory effect in a rat prefused stomach

Test method

JCL-SD male rats (body weight : 300 g) were fasted for 24 hr. prior to the test. Rats were anesthetized with urethane, and the trachea and jugular vein were cannulated. The abdomen was dissected along the median line. Respective perfusion cannulae were inserted into the antrum of stomach and the esophagus and fixed there. A warm physiological saline solution of 37° C. was perfused through the esophagus cannula at the rate of 1 ml/min., and the gastric effluent was collected at a constant interval through the antrum cannula. The perfusate was titrated with 0.01 N NaOH to determine the acid secretion. Acid secretion was continuously stimulated by intravenous infusion of histamine.2HCl (3 mg/kg/hr) through the jugular vein cannula. The test compounds were administered intraperitoneally 90 min. after the histamine and the infusate was further collected for 90 min. for titration as described above to determine the maximal suppression of acid secretion.

Test compounds

Test compounds are shown by compound numbers used in the Examples.

Method of evaluation

Acid secretion suppression rate (%) was calculated from the amount of acid secretion 90 min. after infusion of histamine.2HCl and from the acid secretion at the time of maximal suppression after administration of the test compound.

| | Results | |
|---|---|---|
| Test compd. | Dose (mg/kg) | Antisecretory Effect (%) |
| Ic-1 | 1 | 86 |
| Ic-2 | 10 | 91 |
| Ic-3 | 10 | 98 |
| Ic-6 | 10 | 100 |
| Ic-8 | 10 | 80 |
| Ic-9 | 10 | 100 |
| Ic-12 | 10 | 100 |
| Ic-14 | 3 | 93.1 |
| Ic-15 | 3 | 84.9 |
| Ic-17 | 10 | 100 |
| Ic-23 | 10 | 100 |
| Ic-24 | 3 | 86.3 |
| Cimetidine | 3 | 85 |

From the above results, the compounds (I) of this invention can be said useful as antiulcer agents.

What we claim is:

1. A compound of the formula:

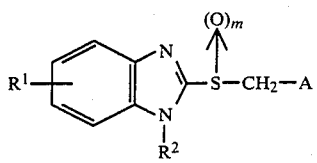 (I)

(wherein $R^1$ is hydrogen, $C_{1-5}$ alkyl, $C_{1-5}$ alkoxy, $C_{1-5}$ alkoxycarbonyl, or trifluoromethyl; $R^2$ is hydrogen, $C_{1-5}$ alkoxycarbonyl, $C_{6-12}$ aryloxycarbonyl, $C_{1-5}$ alkanoyloxy-$C_{1-5}$ alkyl, $C_{1-5}$ alkoxycarboyloxy-$C_{1-5}$ alkyl, $C_{1-5}$ acylamino-$C_{1-5}$ alkyl, 2-hydroxy-1-$C_{2-5}$ alkenyl, phthalimido-$C_{1-5}$ alkyl, halogeno-$C_{1-5}$ alkoxycarbonyl-$C_{1-5}$ alkyl, hydroxy-$C_{1-5}$ alkyl, $C_{1-5}$ alkylthioC-$_{1-5}$ alkyl, or $C_{1-5}$ alkylsulfinyl-$C_{1-5}$ alkyl;

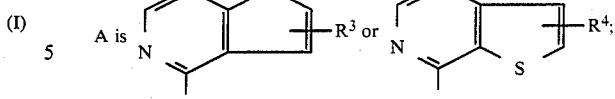

m is an integer of 0 or 1; $R^3$ and $R^4$ each is hydrogen, halogen, cyano, $C_{1-5}$ alkyl, amino, $C_{1-5}$ alkoxy, $C_{6-12}$ aryl-$C_{1-5}$ alkoxy, $C_{1-5}$ alkoxycarbonyl, fluoro-$C_{1-5}$ alkoxy, $C_{1-5}$ alkanoylammino, or carbamoyl) or a pharmaceutical acceptable salt thereof.

2. A compound claimed in claim 1, namely 2-[(3-methylthieno[2, 3-c]pyridin-7-yl)methylsufinyl]benzimidazole.

3. A compound claimed in claim 1, namely 2-[(thieno[2, 3-c]pyridin-7-yl)methylsufinyl]benzimidazole.

4. A pharmaceutical composition for treating a patient suffering from gastric ulcer comprising a pharmacologically effective amount of a compound according to claim 1 together with a carrier, diluent, and/or excipient.

* * * * *